United States Patent
Balsamo et al.

(10) Patent No.: US 8,329,751 B2
(45) Date of Patent: Dec. 11, 2012

(54) COMPOUNDS HAVING ARYL-SULPHONAMIDIC STRUCTURE USEFUL AS METALLOPROTEASES INHIBITORS

(75) Inventors: Aldo Balsamo, Pisa (IT); Armando Rossello, Pisa (IT); Elisa Nuti, Pisa (IT); Elisabetta Orlandini, Pisa (IT); Tiziano Tuccinardi, Livorno (IT)

(73) Assignee: Bracco Imaging S.p.A., Milan (IT)

( * ) Notice: Subject to any disclaimer, the term of this patent is extended or adjusted under 35 U.S.C. 154(b) by 333 days.

(21) Appl. No.: 12/531,119

(22) PCT Filed: Mar. 14, 2008

(86) PCT No.: PCT/EP2008/053078
§ 371 (c)(1),
(2), (4) Date: Sep. 14, 2009

(87) PCT Pub. No.: WO2008/113756
PCT Pub. Date: Sep. 25, 2008

(65) Prior Publication Data
US 2010/0087505 A1    Apr. 8, 2010

(30) Foreign Application Priority Data
Mar. 19, 2007  (EP) .................... 07104393

(51) Int. Cl.
| A61K 31/495 | (2006.01) |
| A61K 31/4035 | (2006.01) |
| A61K 31/18 | (2006.01) |
| C07D 295/088 | (2006.01) |
| C07D 209/48 | (2006.01) |
| C07D 311/48 | (2006.01) |

(52) U.S. Cl. ................. 514/575; 514/488; 514/252.12; 514/417; 544/391; 544/399; 544/400; 548/477; 562/621

(58) Field of Classification Search ................ 514/488, 514/575, 252.12, 417; 544/391, 399, 400; 548/477; 562/621
See application file for complete search history.

(56) References Cited

U.S. PATENT DOCUMENTS
6,673,804 B1 * 1/2004 Kimura et al. ................ 514/274

OTHER PUBLICATIONS
Rosella et al. Bioorganic & Medicinal Chemistry Letters 2005, 15, 2311-2314.*
Rosello et al. Bioorganic & Medicinal Chemistry Letters, 2005, 15, 1321-1326.*
PCT International Search Report for PCT/EP2008/053078, mail date Oct. 20, 2008.
PCT Written Opinion of the International Searching Authority for PCT/EP2008/053078, mail date Oct. 20, 2008.
Rossello, A. et al.; "N-i-Propoxy-N-biphenylsulphonylamino-butylhydroxamic acids as potent and selective inhibitors of MMP- and MT1-MMP"; Bioorganic & Medicinal Chemistry Letters, Mar. 1, 2005, pp. 1321-1326, vol. 15, No. 5, XP004750661, Elsevier Science, Oxford, GB.
Rossello, A. et al.; "A new development of matrix metalloproteinase inhibitors: twin hydroxamic acids as potent inhibitors of MMPs"; Bioorganic & Medicinal Chemistry Letters, May 2, 2005, pp. 2311-2314, vol.15, No. 9, XP004851620, Elsevier Science, Oxford, GB.

* cited by examiner

*Primary Examiner* — Rebecca Anderson
*Assistant Examiner* — Matthew Coughlin
(74) *Attorney, Agent, or Firm* — M. Caragh Noone

(57) ABSTRACT

The invention relates to aryl-sulphonamido compounds endowed with inhibitory activity against metallo proteases MMP, having formula (I) below

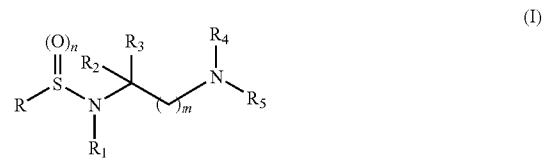

wherein R, $R_1$, $R_2$, $R_3$, $R_4$, $R_5$, n and m have the meanings reported in the specification; the invention also refers to the process for their preparation, to pharmaceutical compositions comprising them and to their use as therapeutic agents, particularly in the treatment of degenerative disorders.

6 Claims, No Drawings

COMPOUNDS HAVING ARYL-SULPHONAMIDIC STRUCTURE USEFUL AS METALLOPROTEASES INHIBITORS

This application is the national stage application of corresponding international application number PCT/EP2008/053078 filed Mar. 14, 2008, which claims priority to and the benefit of the European application no. 07104393.9, filed Mar. 19, 2007, all of which are hereby incorporated by reference.

FIELD OF THE INVENTION

The present invention finds application in the field of therapy and, more in particular, it relates to aryl-sulphonamido compounds, to a process for their preparation, to pharmaceutical compositions comprising them and to their use as therapeutic agents, particularly in the treatment of degenerative disorders.

BACKGROUND

Many physiological and pathological processes are known to be characterised by both a significant hyper-proliferation and mobility of cells. Among them are physiological processes like, for instance, embryogenesis or development and differentiation of tissues and, also, pathological processes among which are tumours or, more in general, disorders affecting a variety of body districts or organs: lungs, muscles, bones, skin as well as the nervous, lymphatic, gastrointestinal, renal, maculo-ocular, cardiovascular system, and the like.

In pathological or non-pathological conditions, high cellular proliferation and mobility mainly depends on the activity of zinc metalloproteases, a class of catalytic proteases present in humans (also referred to as proteinases) which are known to coordinate a zinc ion in their catalytic site, and which are able to hydrolyse amidic bonds within the peptidic chain of the proteins.

Among the zinc metalloproteases are extracellular matrix metalloproteases (hereinafter referred to as MMPs), ADAMS (A Disintegrin and Metalloproteases) and ADAMTs (A Disintegrin and Metalloprotease with Trombospondin Type I repeats).

Once produced, these proteases remain anchored onto the cellular membranes or are excreted in the extra-cellular matrix (ECM), an important physiological structure comprising an organized tri-dimensional network of cells of the surrounding tissues which are electrically, chemically and physically connected to each other.

As such, they may play a key role in several extracellular processes including cell-cell and cell-ECM interactions, as well as in physiological intracellular processes; e.g. growth, development and remodelling of tissues, transduction of intra- and inter-cellular signals and adhesion phenomena.

The proteolytic activity of these zinc metalloproteases, in physiological conditions, is highly and finely tuned by endogenous inhibitors known as tissue inhibitors of metalloproteases (TIMPs), which have been found to exert a fundamental role also in regulating the activity of ADAMs and ADAMTs.

Thus, the delicate equilibrium between MMPs and their inhibitors enables the proper functioning of all of the physiological roles in which MMPs are involved such as, for example, embryonic growth and development, tissue morphogenesis, cell migration and matrix remodelling, reproductive processes, i.e. menstrual cycle and ovulation, bone formation, adipogenesis, wound healing and angiogenesis or even release and processing of bio active molecules as intra- or inter-cellular peptide signals.

Due to their diffusion in the human body and their exerted role, it is thus evident that any alteration in the regulation of even one of the above mentioned processes, for instance because of pathologies like tumours whose progression may determine either over-expression or under-expression of MMPs, would result, almost inevitably, in the occurrence of degenerative processes leading to an abnormal evolution and/or development of tissues.

Examples of the above pathologies in which over- or under-expression of MMPs may be involved, thus leading to an altered tissutal morphology with uncontrolled cell proliferation, may comprise: arthritis and connective tissue disorders; neurodegenerative disorders such as multiple sclerosis, Alzheimer's disease, stroke and ALS (Amyotrophic Lateral Sclerosis); cardiovascular disorders such as atherosclerosis, aneurism, heart failure, dilated cardiomyopathy; pulmonary diseases such as emphysema or cystic fibrosis; gastric ulcers; sepsis and autoimmune disorders.

In addition, during tissutal degeneration, the altered expression of these zinc proteases may also depend, for instance, from the cells type, the activation of their pro-enzymatic forms, genic transcription pathways as well as excretion and endocytosis mechanisms. The extracellular and intracellular threshold of active zinc metalloproteases are often regulated onto the cell membrane surface by means of a catalytic shedding by other metalloproteases like the MMPs anchored onto the cellular membrane, known as Membrane-Type MMPs (MT-MMPS), by Tumor Necrosis Factor alpha convertase, better knows as TACE (and corresponding to ADAM-17), or by even other ADAMs or ADAMTs.

Therefore, for therapeutic purposes, when pathological affections occur as being characterized by a significant activity of metalloproteases on the cell surface of invasive and hyper-proliferating cells, it could be desirable to inhibit those MT-MMPs or some other ADAMs or ADAMTs.

So far, at least 23 different enzymes, which are known to belong to the family of MMPs, have been classified into sub-groups according to their substrate specificity. Among them are, as an example, MMP-1, MMP-8 and MMP-13 known to act on collagenase; MMP-2 and MMP-9, on the other side, known to target gelatinase; and MMP-3, MMP-10 and MMP-11 known to target stromelysin.

In addition, a fourth sub-group of membrane-type MMPs, called as MT-MMPs, have been identified and characterized so far, namely: MT1-MMP (MMP-14), MT2-MMP (MMP-15), MT3-MMP (MMP-16), MT4-MMP (MMP-17), MT5-MMP (MMP-24) and MT6-MMP (MMP-26); the exerted role, however, has been clarified for only some of them (see, for a reference, H G Munshi et al, *Cancer Metastasis Rev.*, 2006, 25, 45-56; and V S Golubkov et al., *J Biol. Chem.*, 2005, 280, 25079-25086).

As an example, MMP-14 is known to be responsible for the activation of pro-MMP-2 on the external surface of some cell types, e.g. smooth muscle cells of vascular tissue in the angiogenetic processes (see, for a reference, N. Koshikawa et al., *J. Cell. Biol.* 2000, 148, 615-624; and Y. Itoh, H. Nagase, *Essays in Biochemistry*, 2002, 38, 21-36).

In addition, MMP-14 is known to be hyper-expressed on the membranes of some types of tumoral cells, such as in melanomas (see, as a reference, N E Sounni et al., *Int. J. Cancer*, 2002, 98, 23-28), breast adenocarcinoma (see, as a reference, N E Sounni, et al., *FASEB J* 2002, 16, 555-564) and in glyomas (A T Belien, et al., *J Cell Biol* 1999, 144, 373-384; and E I Deryugina, et al, *Cancer Res*, 2002; 62:580-588).

MMP-14 may also activate other pro-MMPs like pro-MMP-13, which hyper-expression is known to be correlated, in some cell types, to tumours, inflammation or cardiovascular and neurodegenerative disorders (see, for example, A R Folgueras et al., *Int. J. Dev. Biol.,* 2004, 48, 411-424; and J O Degushi, et al., *Circulation,* 2005, 2708-2715).

Even other MMPs are known to contribute to the activation of pro-MMP-2 and/or pro-MMP-13 and/or pro-MMP9. As an example, MMP-15, MMP-16, MMP-17 and MMP-24 are known to activate pro-MMP-2 and pro-MMP-13; MMP-17 acts only to activate pro-MMP-2, whilst MMP-26 activates pro-MMP-2 and proMMP-9; see, as a reference, A R Folgueras et al., (*Int. J. Dev. Biol.,* 2004, 48, 411-424).

Moreover, MMP-2 and MMP-13 are produced from proliferating and invasive cells and are activated, or anyway activable, in ECM by catalytic activity of the membrane surface MT-MMPs; they represent, therefore, the prior tool for cell motility across the digestive surface permeability of ECM.

Based on previous studies on the so-called "degradomics" (see, as a reference, C Lopez-Otin et al., *Nature Rev.* 2002, 3, 509-519; and C M Overall et al., *Nature Review Cancer,* 2006, 6, 227-239), the possibility of targeting some MMPs as drug delivery candidates for cancer and other pathologies, whilst avoiding interferences with physiological roles exerted by some other MMPs, is nowadays widely acknowledged.

As such, studies are ongoing for the development of MMP inhibitors, to be used in therapy, that are able to selectively address pathological affections without the aforementioned drawbacks.

Therefore, as the activity of some MMPs should be inhibited so as to limit and counteract an occurring degenerative process, the activity of some other types of MMPs regulating physiological processes of development and morphogenesis should not be impaired, as the above may result in undesirable side effects.

Among them is, as an example, the musculoskeletal syndrome with fibroproliferative effects in the join capsule of the knee known to occur upon impairment of the normal tissue remodelling activity exerted by MMP-1. Likewise, the inhibition of some MMPs involved in tumorogenesis control such as, for instance, MMP-3, may cause an increase of cellular proliferation and invasion.

In therapy, therefore, a lack of inhibition on MMP-1 and MMP-3, considered as antitarget, is highly desirable.

On the contrary, an evident selectivity toward MMP-2 and MMP-9 was found to have pro-apoptic effects on tumor cell cultures without showing important side effects.

Therefore, the search for molecules able to specifically regulate the activity of specific MMPs, when normal mechanisms are lost, will provide useful compounds for the treatment of several diseases.

A variety of metalloprotease inhibitors, some of which referring to sulphonamido derivatives, is known in the art.

Among them are, as an example, carbocyclic side chain containing N-substituted metallo protease inhibitors, described in WO 01/70720, and pharmaceutical compositions thereof.

U.S. Pat. No. 6,686,355 discloses biphenyl derivatives possessing a cyclic nitrogen containing sulphonamido group, as MMP inhibitors.

WO 2004/069365 describes diagnostic imaging agents comprising matrix metalloproteases inhibitors bearing substituted N,N-dialkyl chain sulphonamido groups, properly labelled with a γ-emitting radionuclide.

WO 98/39329 describes sulphonamido hydroxamic acid derivatives specifically targeting MMP-2, MMP-9 and MMP-13; the several compounds therein exemplified comprise substituted N,N-dialkyl side chain sulphonamido groups.

U.S. Pat. No. 7,067,670 discloses alkyl-sulphonamido hydroxamic acid derivatives possessing inhibitory activity towards MMP-2 and MMP-13.

U.S. Pat. No. 6,500,948 discloses pyridyloxy- and pyridylthio-arylsulphonamido derivatives having MMP inhibitory activity, wherein the N atom of the sulphonamido group is part of a six membered heterocycle, bearing carbon atoms adjacent to the above N atom.

U.S. Pat. No. 6,495,568 discloses alkyl- or cycloalkyl-sulphonamido hydroxamic acid derivatives as matrix metalloprotease inhibitors.

U.S. Pat. No. 5,985,900 discloses sulphonamido derivatives being characterized by a phenyl- or phenylene-$SO_2NH$— moiety, possessing MMP inhibitory activity.

WO 99/42443 discloses sulfonylamino hydroxamic acid derivatives bearing a group aryl-$SO_2NH$—, therein indicated as matrix-degrading metalloproteinases.

Other sulphonamido MMP inhibitors are known in the art. Among them are selective inhibitors of gelatinase A (MMP-2) being disclosed by Rossello et al. in *Bioorg. & Med. Chem.* 12 (2004) 2441-2450, and having formula (A) below, wherein R is a group selected from isopropyl, allyl or p-(benzyloxy) benzyl.

Likewise, MMP-2 inhibitors showing a good MMP-2/MMP-1 selectivity were also disclosed by Tuccinardi et al (*Bioorg. & Med. Chem.* 14 (2006) 4260-4276); among the exemplified compound therein reported is the derivative of formula (B) below

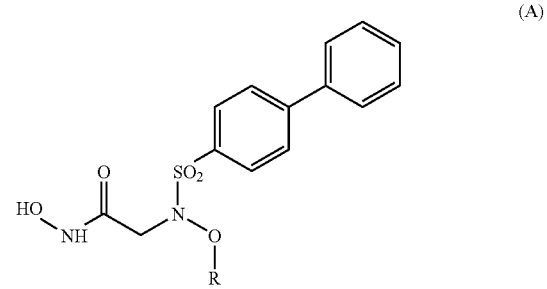

(A)

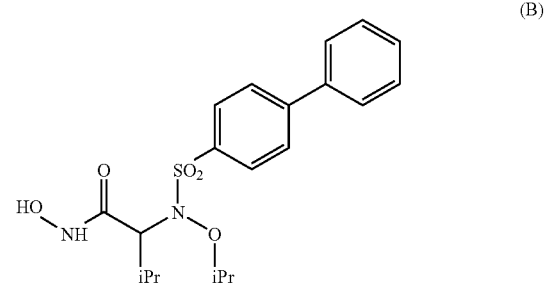

(B)

In addition to the above, previous works in this field have indicated that the use of selective MMP-2 inhibitors that spare some MMPs such as MMP-1 and MMP-3 enables to block invasion of HT1080 cells (of a highly invasive fibrosarcoma) and HUVEC (Human Umbical Vein Endothelial) cells in models of chemoinvasion and angiogenesis (A. Rossello, et al, *Bioorg & Med. Chem.,* 2004, 12, 2441-2450; and A. Rossello, et al., *Bioorg & Med. Chem. Lett.,* 2005, 15, 1321-1326).

As reported in the aforementioned *Bioorg & Med. Chem. Lett.,* (2005), a possible anti-angiogenesis model was developed and specific compounds therein referred to as (5b) and (5c), which formulae are reported below, were synthesized

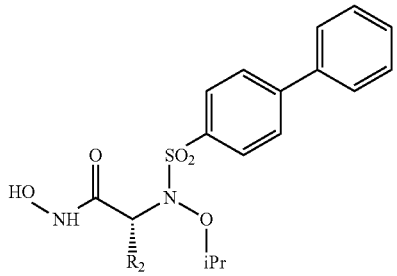

(5b) wherein R$_2$ is ——(CH$_2$)$_2$——NHCOOCH$_2$——C$_6$H$_5$;
(5c) wherein R$_2$ is ——(CH$_2$)$_2$——NH$_2$ Based on the results being obtained on isolated enzymes and according to a method described by C G Knight et al. (see, as a reference, *FEBS Lett.* 1992, 296, 263; and *Methods Enzymol.* 1995, 248, 470), the said method comprising the use of the fluorogenic substrate FS-1 (e.g. Mca-Pro-Leu-Gly-Leu-Dpa-Ala-Arg-NH$_2$) as reported by A. Rossello et al., in Bioorg. Med. Chem. Lett. 12 (2004), 2441-2450, compound (5b) proved to be a dual inhibitor of MMP-2 (IC$_{50}$ value corresponding to 0.41 nM) and of MMP-14 (IC$_{50}$ value corresponding to 7.7 nM).

In this respect, unless otherwise provided and as per the following pharmacological and experimental sections, the above prior art compound (5b) is presently referred to as "Reference Compound (5b)".

Furthermore, the aforementioned Bioorg. Med. Chem. Lett. 15 (2005), 1321-1326, and Bioorg. Med. Chem. Lett. 15 (2005), 2311-2314, disclose chemical synthetic intermediates having the following formulae

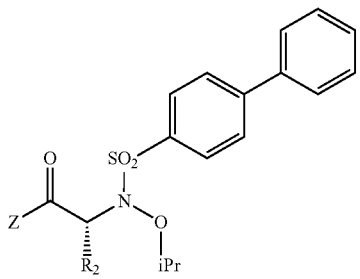

wherein R$_2$ is ——(CH$_2$)$_2$——NH$_2$ or
——(CH$_2$)$_2$——NHCOOCH$_2$——C$_6$H$_5$; and Z is ——OH,
——OC(CH$_3$)$_3$, or NHOCH$_2$C$_6$H$_5$ We have now found a new class of zinc metalloprotease inhibitors having aryl-sulphonamidic structure which, based on IC$_{50}$ values of inhibition tests being in the nano/subnano molar range, resulted to be particularly effective towards target enzymes, in particular MMP-2, MMP-13 and MMP-14.

OBJECT OF THE INVENTION

Therefore, it is a first object of the present invention a compound having the following general formula (I)

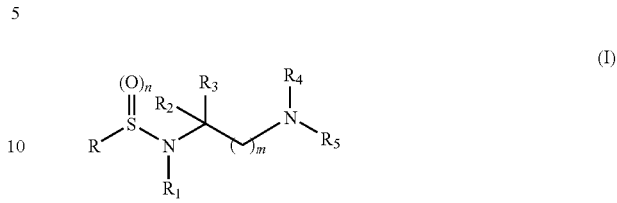

wherein:
R is a group of formula —Ar—X—Ar' (II) wherein Ar is an arylene, heteroarylene, aryl or heteroaryl group and Ar', the same or different and independently from Ar, is an aryl or heteroaryl group or H; the said Ar and Ar' being optionally substituted by one or more groups selected from:
  (i) straight or branched alkyl, alkoxy, hydroxyalkyl, alkoxyalkyl, aminoalkyl, alkylamino, aminoacyl, acylamino or perfluorinated alkyl, each of which having from 1 to 4 carbon atoms in the alkyl chain;
  (ii) straight or branched C$_2$-C$_6$ alkenyl or alkynyl group;
  (iii) halogen or a cyano (—CN) group;
X is a single bond or it is a divalent linker selected from a straight or branched C$_1$-C$_4$ alkylene chain, —O—, —S—, —S(O)$_2$—, —CO—, —NR'—, —NR'CO— or —CONR'—, wherein R' is H or a straight or branched C$_1$-C$_4$ alkyl group;
R$_1$ is —OH or a group —ORa wherein Ra is selected from straight or branched C$_1$-C$_4$ alkyl or C$_2$-C$_4$ alkenyl groups; or Ra is a group of formula (III)

—(CH$_2$)$_p$—Z—(CH$_2$)$_r$—W    (III)

wherein p is zero or an integer from 1 to 4; Z is a single bond or a divalent linker selected from —O—, —NR'—, —NR'CO— or —CONR'—, wherein R' is as above defined; r is zero or an integer from 1 to 4; and W is phenyl or a 5 or 6 membered heterocycle, each of which being optionally substituted by one or more groups selected from —NH$_2$, —COR', —CONHR', —COOR' or —SO$_2$NHR' wherein R' is as above defined, by aryl or heteroaryl or by one or more of the above groups from (i) to (ii);
R$_2$ and R$_3$ are, the same or different and each independently, H, a straight or branched C$_1$-C$_4$ alkyl group optionally substituted by hydroxyl or C$_1$-C$_4$ alkoxy groups, or a zinc binding group selected from —COOH, —COORb, —CONHOH, —CONHORb, —CONRbOH, —CONHS(O)$_2$Rb, —CONH$_2$, —CONHRb or —P(O)(OH)$_2$, wherein Rb is a straight or branched alkyl, arylalkyl or heteroarylalkyl group having from 1 to 4 carbon atoms in the alkyl chain; or any of the above R$_2$ or R$_3$ groups is linked to R$_1$ so as to form a 5 to 7 membered heterocyclic ring at least comprising two adjacent N—O heteroatoms, optionally substituted by one or more oxo groups (═O);
R$_4$ is H or a group selected from —CORc, —COORc, —S(O)$_2$Rc, —CONHRc or —S(O)$_2$NHRc, wherein Rc is a group selected from C$_3$-C$_6$ cycloalkyl, straight or branched alkyl, aryl, heteroaryl, arylalkyl, heteroarylalkyl, alkylaryl, alkylheteroaryl, a 5 or 6 membered heterocyclyl, alkylheterocyclyl or heterocycloalkyl having from 1 to 4 carbon atoms in the alkyl chain;
R$_5$ is H or, together with the N atom to which they are bonded, R$_4$ and R$_5$ form an optionally benzocondensed 4 to 6 membered heterocycle, optionally substituted by a group Ra as above defined and/or by one or more oxo (═O) groups;
n is 1 or 2;
m is an integer from 1 to 6;

provided that when R is biphenyl-4-yl, $R_1$ is isopropoxy, m and n are both 2, $R_5$ is H, one of $R_2$ or $R_3$ is —COOH, —COOC(CH$_3$)$_3$, —CONHOH or —CONHOCH$_2$C$_6$H$_5$ and the remaining one of $R_2$ or $R_3$ is H, then $R_4$ is not H or benzyloxycarbonyl;

and the pharmaceutically acceptable salts thereof.

The compounds of formula (I) may have one or more asymmetric carbon atom, otherwise referred to as chiral carbon atom, and may thus exist in the form of single enantiomers, racemates, diastereoisomers and any mixture thereof, all to be intended as comprised within the scope of the present invention.

As set forth above, within the compounds of formula (I) of the invention, R is a group of formula —Ar—X—Ar' (II) wherein Ar represents an arylene or heteroarylene group linked to —X—Ar' or, when X represents a single bond and Ar' is H, an aryl or heteroaryl group.

In this context, despite the fact that arylene and heteroarylene are presently intended so as to define a divalent radical group (e.g. phenylene —C$_6$H$_4$—), both terms aryl and arylene (and thus heteroaryl and heteroarylene) are herewith used interchangeably unless otherwise provided.

In the present description, and unless otherwise provided, with the term aryl group (and thus of arylene group) we intend a carbocyclic aromatic group.

With the term heteroaryl (and thus heteroarylene) we intend a 5 or 6 membered aromatic heterocycle with from 1 to 3 heteroatoms or heteroatomic groups selected from N, NH, O or S.

Suitable examples of aryl of heteroaryl groups, when referring to Ar and Ar' and, also, to any other aryl or heteroaryl group being present within the compounds of formula (I), may thus include phenyl, pyrrolyl, furyl, thienyl, pyrazolyl, imidazolyl, oxazolyl, isoxazolyl, pyridyl, pyrimidinyl, thiazolyl, and the like.

As far as formula (II) is concerned, it is clear to the skilled person that both Ar and Ar' may be directly linked to each other, when X represents a single bond so as to give rise to a group —Ar—Ar' or, alternatively, they may be linked to each other through any suitable divalent linker among those above indicated thus providing, as an example, R groups corresponding to —Ar—O—Ar', —Ar—S—Ar', —Ar—CONR'—Ar', and the like.

In addition, and when referring to Ar' as corresponding to a hydrogen atom H, any of the above R groups could be identified, respectively, by —Ar itself (when X is a bond) or by a group —Ar—OH, —Ar—SH, —Ar—CONR'H, and the like.

As formerly reported, any of the above Ar and/or Ar' groups may be optionally further substituted, in any free position, by one or more groups as defined in items from (i) to (iii).

Among the optional substituents, and unless otherwise provided, with straight or branched alkyl with from 1 to 4 carbon atoms in the chain we intend any of the $C_1$-$C_4$ alkyl groups thus including methyl, ethyl, n-propyl, isopropyl, n-butyl, isobutyl, sec-butyl and tert-butyl.

Likewise, when referring to alkoxy we intend any of the corresponding alkyl-oxy groups such as methoxy, ethoxy, n-propoxy, isopropoxy, and the like.

From the above, the alkyl groups may be further substituted by hydroxyl (—OH), amino (—NH$_2$) or even by the aforementioned alkoxy (—OAlk) groups so as to give rise to hydroxyalkyl (HO-Alk-), aminoalkyl (H$_2$N-Alk-) or alkoxyalkyl (Alk-O-Alk) groups, respectively.

By analogy, with the terms alkylamino we refer to an amino group being further substituted by any of the aforementioned alkyl groups, so as to give rise to Alk-NH— groups.

With the term acyl, unless otherwise provided, we intend any of the groups conventionally identifiable as Alk(CO)— groups wherein the Alk residue just represents any straight or branched $C_1$-$C_4$ alkyl group.

Suitable examples of acyl groups may thus include acetyl (CH$_3$CO—), propionyl (CH$_3$CH$_2$CO—), butirryl [CH$_3$(CH$_2$)$_2$CO—], isobutirryl [(CH$_3$)$_2$CHCO—], valeryl [CH$_3$(CH$_2$)$_3$CO—], and the like.

From the above, aminoacyl groups may thus include H$_2$NCO— as well as any of the above acyl groups wherein the alkyl chain is properly substituted by amino such as, for instance, aminoacetyl (H$_2$NCH$_2$CO—), aminopropionyl [H$_2$NCH$_2$CH$_2$CO— or CH$_3$CH(NH$_2$)CO—], and the like.

By analogy, unless otherwise provided, acylamino groups may be suitably represented by carboxamido groups wherein any of the former acyl groups is bonded to —NH— such as, for instance, acetamido (CH$_3$CONH—), propionamido (CH$_3$CH$_2$CONH—), butirramido [CH$_3$(CH$_2$)$_2$CONH—], and the like.

With the term perfluorinated alkyl we intend any of the former alkyl groups wherein all of the hydrogen atoms are replaced by fluorine atoms like, for instance, trifluoromethyl, —C$_2$F$_5$, —C$_3$F$_7$ or —C$_4$F$_9$ groups.

With the term straight or branched $C_2$-$C_6$ alkenyl or alkynyl group we intend any of the $C_2$-$C_6$ hydrocarbon chains comprising at least one double bond or triple bond, respectively.

Suitable examples of alkenyl or alkynyl groups according to the invention thus comprise vinyl, allyl, propenyl, isopropenyl, butenyl, isobutenyl, hexenyl, ethynyl, propynyl, butynyl, and the like.

Finally, with the term halogen atom we intend any of the fluorine, chlorine, bromine or iodine atoms.

According to a first embodiment of the invention, within the compounds of formula (I), R represents a group of formula (II) wherein Ar represents an optionally substituted phenylene group, X represents a single bond or a divalent linker selected from —O—, —S— or —NH— and Ar' represents H or an optionally substituted phenyl group.

Preferred substituents, in this class, are straight or branched $C_1$-$C_4$ alkyl or alkoxy groups or halogen atoms.

Even more preferably, within the compounds of formula (I), R represents a group of formula (II) wherein Ar represents a phenylene group, X represents a single bond or —O— and Ar' represents H or a phenyl group, the phenylene and phenyl groups being optionally substituted by straight or branched $C_1$-$C_4$ alkyl or alkoxy groups or by halogen atoms.

Still more preferred, within this class, are the compounds of formula (I) wherein R is a group selected from biphenyl-4-yl, 4-bromophenyl, 4-(4'-methoxyphenyl)-phenyl, 4-(4'-ethoxyphenyl)-phenyl, 4-phenoxy-phenyl, 4-(4'methoxyphenoxy)-phenyl and 4-(4'ethoxyphenoxy)-phenyl According to a different aspect of the invention, within the compounds of formula (I), $R_1$ is a group —OH or —ORa wherein Ra is alkyl or alkenyl or it is a group of formula (III) wherein p, Z and r are as above defined and W is phenyl or a 5 or 6 membered heterocycle, each of which being optionally further substituted as above indicated.

In the present description, and unless otherwise provided, with the term 5 or 6 membered heterocycle or heterocyclic group we intend any 5 or 6 membered aromatic or non aromatic heterocycle, hence including saturated, partly unsaturated or even fully unsaturated rings, with from 1 to 3 heteroatoms or heteroatomic groups selected from N, NH, O or S.

From the above, it is clear to the skilled person that the aforementioned definition of heterocycle or heterocyclic group also encompasses any fully unsaturated heterocycle, also known as heteroaryl group.

Suitable examples of heterocyclic groups, not including those already reported as falling within the definition of heteroaryl, may thus comprise tetrahydrofuran, pyrroline, pyrrolidine, morpholine, thiomorpholine, piperidine, piperazine, and the like.

According to a preferred embodiment of the invention, within the compounds of formula (I), $R_1$ is a group —ORa, wherein Ra is an alkyl or alkenyl group as above defined, or it is a group of formula (III) wherein p is 1 or 2, Z is a single bond or a divalent group selected from —O— or —NH—, r is 0, 1 or 2, and W is an optionally substituted phenyl or heterocyclic group as above defined.

Still more preferred, within this class, are the compounds of formula (I) wherein $R_1$ is selected from isopropoxy, benzyloxy, 4-phenyl-benzyloxy, allyloxy, 2-[2(piperazinyl-1-yl)ethoxy]ethoxy or 2-[2(4(ethylcarbonyl)piperazinyl-1-yl)ethoxy]ethoxy.

As far as $R_2$ and $R_3$ are concerned, in formula (I), they independently represent H, an optionally substituted alkyl group or a zinc binding group among those formerly reported.

Alternatively, $R_2$ or $R_3$ may be linked to $R_1$ so as to give rise to a 5 to 7 membered heterocyclic ring at least comprising two adjacent N—O heteroatoms, e.g. the N atom being bonded to S, in formula (I), and the O atom being part of $R_1$ itself.

As a non limiting example, suitable compounds of formula (I) wherein one of $R_2$ or $R_3$ (e.g. $R_2$) is linked to $R_1$ so as to give rise to the above heterocyclic structures may thus comprise:

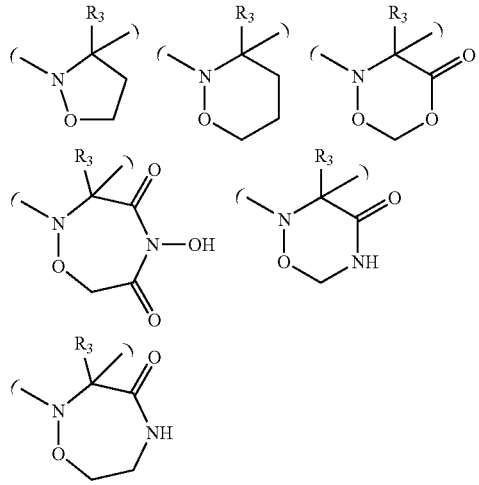

wherein the above adjacent N—O heteroatoms are represented in bold.

According to a preferred embodiment of the invention, $R_2$ and $R_3$ are selected, each independently, from H, straight or branched $C_1$-$C_4$ alkyl, —COOH, —COORb, —CONHOH or —CONHORb, wherein Rb is a straight or branched alkyl, arylalkyl or heteroarylalkyl group having from 1 to 4 carbon atoms in the alkyl chain.

Still more preferably, within this class, $R_2$ and $R_3$ are both H atoms or one of them is H and the remaining one of $R_2$ or $R_3$ is —COOH or —CONHOH.

With respect to the meanings of $R_4$, the said group may represent a hydrogen atom H or a carbonyl, carboxyl, sulphonyl, carboxamido or sulphonamido group, further derivatized through the above indicated Rc groups.

When referring to Rc, and unless otherwise provided, with the term $C_3$-$C_6$ cycloalkyl we intend any 3 to 6 membered cycloaliphatic ring such as cyclopropyl, cyclobutyl, cyclopentyl and cyclohexyl.

From the above, having defined the meanings of alkyl, aryl, heteroaryl and heterocycle (or heterocyclyl), any composite-name group such as arylalkyl, alkylaryl, heteroarylalkyl, alkylheteroaryl, alkylheterocyclyl or heterocyclylalkyl, should be clear to the skilled person.

Just as an example, and unless otherwise provided, with the term alkylaryl we intend any aryl group further substituted by alkyl: e.g. p-ethyl-phenyl (p$C_2H_5$—$C_6H_4$—); with the term arylalkyl we instead refer to an alkyl group further substituted by aryl: e.g. 2-phenyl-ethyl ($C_6H_5$—$CH_2$—$CH_2$—); and the like.

From all of the above it should be clear to the skilled person that analogous consideration may apply for heteroarylalkyl, alkylheteroaryl, heterocycloalkyl or alkylheterocyclyl groups.

With respect to $R_5$, in formula (I), it represents H or, alternatively, $R_4$ and $R_5$ together with the N atom to which they are bonded form an optionally benzocondensed 4 to 6 membered heterocycle, as above reported.

Suitable examples of the said heterocycles, for instance substituted by Ra and oxo groups, may thus comprise:

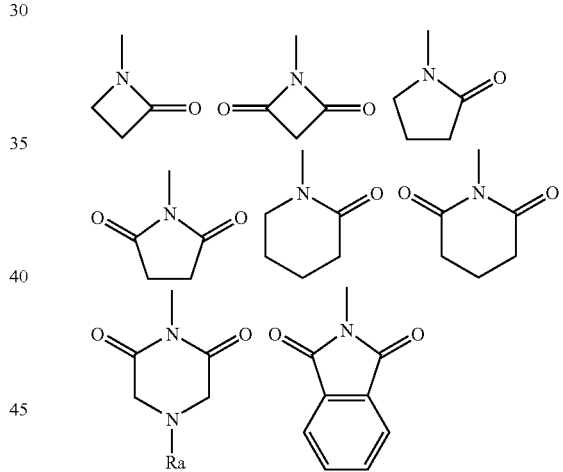

According to an additional preferred embodiment of the invention, $R_4$ is selected from —CORc, —COORc or —S(O)$_2$Rc, wherein Rc is aryl, straight or branched alkyl or an arylalkyl group having from 1 to 4 carbon atoms in the alkyl chain; and $R_5$ is H.

Even more preferred, within this class, are the compounds of formula (I) wherein $R_4$ is selected from acetyl, benzoyl, phenacetyl, 4-phenylbutanoyl, benzyloxycarbonyl, methanesulphonyl, phenylsulphonyl or benzylsulphonyl, and $R_5$ is H.

According to a still different embodiment of the invention, $R_4$ and $R_5$ together with the N atom to which they are bonded, form an N-phthalimido group.

Finally, according to an additional preferred embodiment of the invention, within the compounds of formula (I), n and m are both 2.

As formerly reported, the compounds of formula (I) of the invention can also be present in the form of a pharmaceutically acceptable salt.

The term "pharmaceutically acceptable salt", as used herein, refers to derivatives of the compounds of the invention wherein the parent compound is suitably modified by converting any of the free acid or basic groups, if present, into the corresponding addition salt with any base or acid conventionally intended as being pharmaceutically acceptable.

Apart from being non-toxic, the corresponding salts of the compounds of formula (I) of the invention are also characterized by a high stability, including a physiological stability upon usage and administration.

Suitable examples of the said salts may thus include mineral or organic acid addition salts of basic residues such as amino groups, as well as mineral or organic basic addition salts of acidic residues such as carboxylic, phosphonic or sulphuric groups. Preferred cations of inorganic bases which can be suitably used to prepare salts within the invention comprise ions of alkali or alkaline-earth metals such as potassium, sodium, calcium or magnesium. Preferred cations of organic bases comprise, inter alia, those of primary, secondary and tertiary amines such as ethanolamine, diethanolamine, morpholine, glucamine, N-methylglucamine, N,N-dimethylglucamine.

Preferred anions of inorganic acids which can be suitably used to salify the compounds of the invention comprise the ions of halo acids such as chlorides, bromides, iodides or other suitable ions such as sulfates.

Preferred anions of organic acids comprise those routinely used in pharmaceutical techniques for the salification of basic substances such as, for instance, acetate, trifluoroacetate, succinate, citrate, fumarate, maleate or oxalate.

Preferred amino acids that can be suitably used to salify the compounds of the invention may also comprise, for instance, taurine, glycine, lysine, arginine, ornithine, aspartic and glutamic acid.

Specific examples of the compounds of formula (I) of the invention, together with the process for their preparation, are reported in the following experimental section.

The process for the preparation of the compounds of the invention may be carried out according to conventional methods well known to those skilled in synthetic organic chemistry techniques.

Therefore, it is an additional object of the invention a process for the preparation of the compounds of formula (I), which process comprises:
a) reacting a compound of formula (IV) with a compound of formula (V)

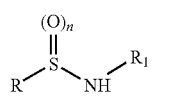

(IV)

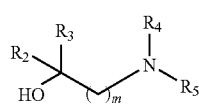

(V)

wherein R, $R_1$, $R_2$, $R_3$, $R_4$, $R_5$, n and m have the above reported meanings so as to obtain a compound of formula (I) of the invention; and, optionally
b) converting the compound of formula (I) being obtained in step (a) into another compound of formula (I) and/or into a pharmaceutically acceptable salt thereof.

The above process is particularly advantageous as it is susceptible of being properly modulated, through any proper variant, so as to obtain any of the desired compounds of formula (I).

In step (a) of the process, the reaction between the compounds of formula (IV) and (V) is carried out according to conventional methods for the preparation of sulphonamido or sulphinamido groups with n as 2 or 1, respectively.

Typically, the reaction is carried out under the known Mitsunobu condensation operative conditions, in the presence of suitable solvents including, among others, tetrahydrofuran, dichloromethane, acetonitrile, N-methylpyrrolidone, benzene, toluene, m-xylene, and mixtures thereof.

In this respect, the above reaction may take place in the presence of a suitable condensing agent, either as such or suitably supported onto polymeric resins and including, for instance, diethyl azodicarboxylate (DEAD), diisopropylazodicarboxylate (DIAD), 1,1'-azodicarbonyldipiperidine (ADDP), N,N,N',N'-tetramethylazodicarboxamide (TMAD), triphenylphosphine ($PPh_3$), tributylphosphine ($PBu_3$), and the like.

From all of the above, it should be clear to the skilled person that, in step (a) of the process, any of the R, $R_1$, $R_2$, $R_3$, $R_4$ and $R_5$ groups, hereinafter shortly referred to as "R" groups, may be present as such or, alternatively, may be present in any properly protected form.

More in particular, functional groups being present in any of the compounds of formula (IV) or (V) and which could give rise to unwanted side reactions and by-products, need to be properly protected before the condensation reaction takes place. Likewise, subsequent deprotection of those same protected groups may follow upon completion of the said reactions.

In the present invention, unless otherwise indicated, the term "protecting group", designates a protective group adapted to preserving the function of the group to which it is bound. Specifically, protective groups are used to preserve amino, hydroxyl or carboxyl functions. Appropriate protective groups may thus include, for example, benzyl, benzyloxycarbonyl, alkyl or benzyl esters, or other substituents commonly used for the protection of such functions, which are all well known to those skilled in the art [see, for a general reference, T. W. Green; Protective Groups in Organic Synthesis (Wiley, N.Y. 1981)].

Likewise, selective protection and deprotection of any of the said groups, for instance including carboxyl, hydroxyl and amino groups, may all be accomplished according to very well known methods commonly employed in organic synthetic chemistry.

In addition to the above, as per step (b) of the process, any of the "R" groups within the final compounds of formula (I) that could be easily identified as a derivatized group, for instance any ester or amide, may be prepared from the functional groups from which it derives, by working according to conventional methods.

As a non limiting example, for instance in the case of the preparation of a compound of formula (I) wherein $R_2$ is a group —COORb, Rb is an alkyl group and $R_3$ is H, that same compound could be prepared according to the present process: (i) by starting from a compound of formula (V) wherein $R_2$ and $R_3$ are as above defined, as per step (a); or, alternatively, (ii) by starting from a corresponding compound of formula (I) wherein $R_2$ is —COOH, and by properly converting the carboxyl group into the desired —COORb group, as per step (b) of the process.

The above reaction conditions are well known in the art for the preparation of carboxylic esters.

Analogous considerations may apply, for instance, in the preparation of carboxamides by properly reacting the corresponding carboxyl derivative with any suitable amine, and by working according to well known operative conditions.

Likewise, for instance in the preparation of a compound of formula (I) wherein $R_2$ is the hydroxamic group —CONHOH, the process may be carried out by first reacting a compound of formula (I) wherein $R_2$ is carboxyl, being obtained in step (a), in the presence of suitable reactants like, for instance, O-(tert-butyldimethylsilyl)hydroxylamine, O-(tetrahydro-2H-pyran-2-yl)hydroxylamine, O-tritylhydroxylamine or O-benzylhydroxylamine, as the case may be.

Subsequent deprotection of the obtained intermediate derivative, for instance under acidic hydrolysis in the presence of trifluoroacetic acid or with trimethylsilyltriflate or by catalytic hydrogenation in the case of O-benzylhydroxylamine, may lead to the desired compound with $R_2$ as —CONHOH.

Several additional examples are known in the art as allowing to convert a given group within a compound of formula (I) into another group. They may comprise, for instance: the conversion of an amino (—$NH_2$) or caroboxamido ($CONH_2$) group into the corresponding N-substituted derivative; the conversion of a carboxyl group into the corresponding benzyl ester derivative, by reaction with benzylbromide in the presence of cesium carbonate, as per well known operative conditions; the conversion of a carboxyl group (—COOH) into the corresponding (—$CONHSO_3H$) group, by its first conversion into (—$CONH_2$) followed by reaction with chlorosulfonic acid in the presence of 2-picoline; the conversion of a carboxyl group (—COOH) into the corresponding [—$CH_2PO(OH)_2$] group, by its first reduction to hydroxymethyl (—$CH_2OH$), subsequent conversion into (—$CH_2Cl$) by means of thionyl chloride, followed by reaction with triethylphosphite to give the corresponding [—$CH_2P(OH)_2$] group finally hydrolyzed to [—$CH_2PO(OH)_2$].

All of the above reactions and operative conditions thereof are well known in the art and allow to obtain a variety of compounds of formula (I).

Clearly, also per step (b) of the process, any functional group within the compounds of formula (I) being obtained in step (a) and that could lead to undesired by-products, need to be properly protected before the reaction takes place, and then deprotected, according to known methods.

For a reference to the specific operative conditions being employed in the preparation of the compounds of formula (I) see, as an example, the following Scheme 1 that provides synthetic pathways for the preparation of representative compounds of the invention. Specific details, however, can be found in the experimental section.

Within the Scheme 1 below, it is reported the preparation of some representative compounds of formula (I) of the invention wherein n and m are both 2; R, $R_1$ and $R_4$ have the meanings therein reported, one of $R_2$ or $R_3$ is H and the remaining one of $R_2$ or $R_3$ is a carboxyl or hydroxamic group (—COOH or —CONHOH) and $R_5$ is H.

Scheme 1

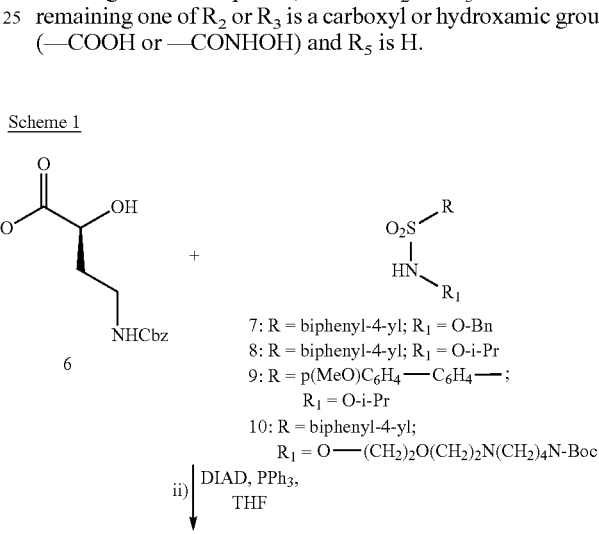

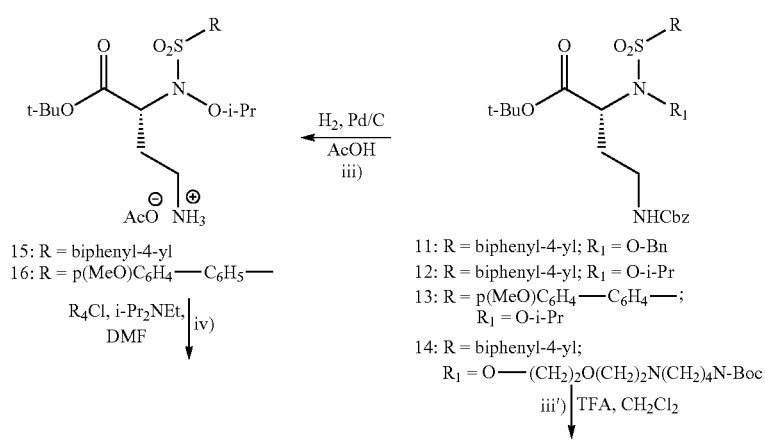

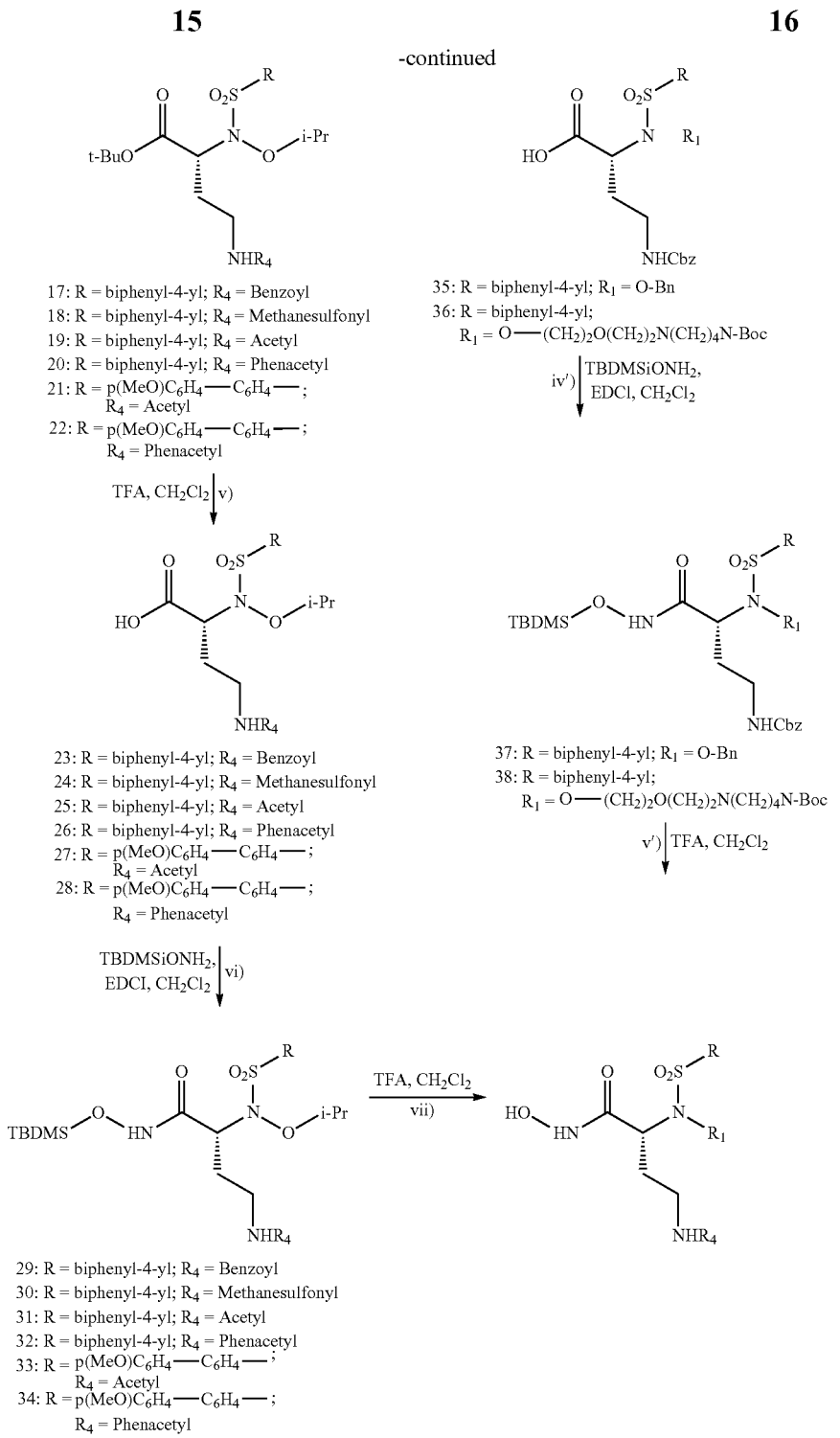

17: R = biphenyl-4-yl; R₄ = Benzoyl
18: R = biphenyl-4-yl; R₄ = Methanesulfonyl
19: R = biphenyl-4-yl; R₄ = Acetyl
20: R = biphenyl-4-yl; R₄ = Phenacetyl
21: R = p(MeO)C₆H₄—C₆H₄—;
    R₄ = Acetyl
22: R = p(MeO)C₆H₄—C₆H₄—;
    R₄ = Phenacetyl 23: R = biphenyl-4-yl; R₄ = Benzoyl
24: R = biphenyl-4-yl; R₄ = Methanesulfonyl
25: R = biphenyl-4-yl; R₄ = Acetyl
26: R = biphenyl-4-yl; R₄ = Phenacetyl
27: R = p(MeO)C₆H₄—C₆H₄—;
    R₄ = Acetyl
28: R = p(MeO)C₆H₄—C₆H₄—;
    R₄ = Phenacetyl 29: R = biphenyl-4-yl; R₄ = Benzoyl
30: R = biphenyl-4-yl; R₄ = Methanesulfonyl
31: R = biphenyl-4-yl; R₄ = Acetyl
32: R = biphenyl-4-yl; R₄ = Phenacetyl
33: R = p(MeO)C₆H₄—C₆H₄—;
    R₄ = Acetyl
34: R = p(MeO)C₆H₄—C₆H₄—;
    R₄ = Phenacetyl 35: R = biphenyl-4-yl; R₁ = O-Bn
36: R = biphenyl-4-yl;
    R₁ = O—(CH₂)₂O(CH₂)₂N(CH₂)₄N-Boc 37: R = biphenyl-4-yl; R₁ = O-Bn
38: R = biphenyl-4-yl;
    R₁ = O—(CH₂)₂O(CH₂)₂N(CH₂)₄N-Boc Essentially, the above preparation process comprises the steps of:

i) protecting the carboxyl group of compound (5) with any suitable protecting group, for instance with N,N-dimethylformamide di-tert-butyl acetal in toluene (see, as a general reference, Rossello et al. *Bioorg. Med. Chem. Lett,* 2005, 15, 1321), thus providing the compound of formula (6);

ii) reacting any one of the compounds (7-10) with the compound of formula (6) by working according to well known Mitsunobu operative conditions, for instance in the presence of diisopropylazodicarboxylate (DIAD) and triphenylphosphine (PPh₃) as condensing agents, in a suitable solvent like tetrahydrofuran, thus obtaining the corresponding compounds of formula (11-14); and processing them as per the alternative pathways below:

iii) deprotecting the amino group of the compounds (12-13) according to conventional methods including, for instance, catalytic hydrogenation with palladium or platinum catalysts in acetic acid, so as to obtain the compounds (15-16);

iv) properly functionalizing the amino group of compounds (15-16) so as to get any desired —NHR$_4$ group, as per compounds (17-22), for instance through reaction with any suitable acylating agent;

v) deprotecting the carboxylic function so as to get the corresponding compounds (23-28) under suitable hydrolysis conditions, for instance in the presence of trifluoroacetic acid and in a suitable solvent like dichloromethane;

vi) converting that same carboxylic group of compounds (23-28) into a suitable silyl derivative (29-34) according to known methods, for instance by means of O-(tert-butyldimethylsilyl)hydroxylamine in dichloromethane, followed by the addition of 1-[3-(dimethylamino)propyl]-3-ethyl carbodiimide;

vii) and hydrolysing compounds (29-34), for instance with trifluoroacetic acid in dichloromethane, so as to lead to the desired compounds of formula (I);

or, alternatively iii') deprotecting the carboxylic function of compounds (11 and 14) so as to obtain the compounds (35 and 36), for instance by working as per step (v);

iv') converting the compounds thus obtained to the corresponding silyl derivatives (37-38), for instance by working as per step (vi);

v') and hydrolysing compounds (37-38), for instance by working as per step (vii), thus obtaining the desired compounds of formula (I).

Finally, optional salification of the compounds of formula (I) may be carried out by properly converting any of the free acidic groups (e.g. carboxylic, sulforic, phosphonic and the like) or free amino groups into the corresponding pharmaceutically acceptable salts. In this case too, the operative conditions being employed for the optional salification of the compounds of the invention are all within the ordinary knowledge of the skilled person.

From all of the above, it should be clear to the skilled person that the above process, comprehensive of any variant thereof for the preparation of suitable compounds of formula (I) of the invention, may be conveniently modified so as to adapt the reaction conditions to the specific needs, for instance by choosing appropriate condensing agents, solvents and protective groups, as the case may be.

The compounds of formula (IV) and (V), as starting materials of the present process, are known or can be easily prepared according to known methods.

The sulphonamido derivatives of formula (IV), for instance, may be prepared by reacting any suitable amino compound with any suitable sulphonyl chloride derivative, substantially as follows:

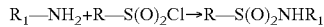

Likewise, if not known per se, both the above amine and the sulphonyl chloride derivative may be easily prepared according to known methods from commercially available compounds.

Analogous consideration may apply to the compounds of formula (V) that, if not commercially available per, se may be conveniently prepared according to conventional methods well known in the art.

Pharmacology
Inhibitory Activity

According to the present invention, the compounds of formula (I) are endowed with inhibitory activity against matrix metalloproteases and are therefore useful, in therapy, in the treatment of pathologies in which the regulation of said enzymes is altered. More in particular, the compounds were tested to prove their activity against MMP-2, MMP-13 and MMP-14, according to the method described in Example 16.

As reported therein, the inhibitory activity of the compounds of the invention was evaluated on the known fluorogenic substrate (Mca-Lys-Pro-Leu-Gly-Leu-Dpa-Ala-Arg-NH$_2$), shortly referred to as FS-6 (see, as a reference, U. Neumann, *Analytical Biochem.* 2004, 328, 166-173).

The said fluorogenic substrate was developed from the analogous FS-1 (see, as a reference, the aforementioned CG Knight et al., in *Febs Lett.* 1992, 296, 263-266) through the insertion of a lysine residue between Mca and Proline residues.

As the elongation of the peptide chain, in FS-6, was reported as improving the ability of the substrate to be hydrolyzed by MMPs, presumably because of the sterically hindered Mca moiety that might have been responsible for the decreased substrate affinity for some MMPs, present compounds were tested according to this more accurate and highly sensible method, based on FS-6.

Therefore, as per the experimental data thus obtained and comments thereof (see Example 16), the compounds of the invention resulted to be endowed with an inhibitory activity against MMP-2, MMP-13 and MMP-14, markedly superior than that of the structurally close prior art compound, presently identified as Reference Compound (5b). Because of their unexpected activity profile, therefore, the compounds of the invention may be advantageously used, in therapy, in the treatment of those pathologies broadly referred to as degenerative disorders, wherein the above enzymes are involved.

According to this latter aspect, the compounds of formula (I) for therapeutic purpose are those formerly reported and also include the aforementioned prior art compounds disclosed as chemical intermediates only.

Therefore, it is an additional embodiment of the invention a compound of formula (I) wherein R, R$_1$, R$_2$, R$_3$, R$_4$, R$_5$, n and m are as set forth above, with the proviso that when R is biphenyl-4-yl, R$_1$ is isopropoxy, m and n are both 2, R$_5$ is H, one of R$_2$ or R$_3$ is —CONHOH and the remaining one of R$_2$ or R$_3$ is H, then R$_4$ is not H or benzyloxycarbonyl; and the pharmaceutically acceptable salts thereof, for use as a medicament.

Additionally, also comprised within the scope of the invention is the use of the above compounds of formula (I) wherein R, R$_1$, R$_2$, R$_3$, R$_4$, R$_5$, n and m are as set forth above, with the proviso that when R is biphenyl-4-yl, R$_1$ is isopropoxy, m and n are both 2, R$_5$ is H, one of R$_2$ or R$_3$ is —CONHOH and the remaining one of R$_2$ or R$_3$ is H, then R$_4$ is not H or benzyloxycarbonyl, and the pharmaceutically acceptable salts thereof, in the preparation of a medicament for the treatment of degenerative disorders.

The said degenerative disorders comprise tumours and, more in general, pathologies leading to an altered tissual morphology with uncontrolled cell proliferation.

The said pathologies may thus comprise: arthritis and connective tissue disorders; neurodegenerative disorders such as multiple sclerosis, Alzheimer's disease, stroke and ALS (Amyotrophic Lateral Sclerosis); cardiovascular disorders such as atherosclerosis, aneurism, heart failure, dilated cardiomyopathy; pulmonary diseases such as emphysema or cystic fibrosis; gastric ulcers; sepsis and autoimmune disorders.

In a still another embodiment, the invention concerns pharmaceutical compositions comprising, as an active ingredient, a pharmaceutically effective amount of a compound of formula (I), wherein R, R$_1$, R$_2$, R$_3$, R$_4$, R$_5$, n and m are as set forth above, with the proviso that when R is biphenyl-4-yl, R$_1$ is isopropoxy, m and n are both 2, $R_5$ is H, one of $R_2$ or $R_3$ is —CONHOH and the remaining one of $R_2$ or $R_3$ is H, then $R_4$ is not H or benzyloxycarbonyl, and the pharmaceutically acceptable salts thereof, in combination with one or more pharmaceutically acceptable carriers, diluents or excipients.

The compositions of the invention can be well prepared according to conventional methods widely known in the art for the preparation of pharmaceutical forms and may comprise any of the carriers, diluents or excipients known in the art for the intended purpose.

In a yet another aspect, the invention provides a method for the treatment of the above degenerative disorders, which method comprises the administration, to a mammal in need thereof, of a therapeutically effective amount of a compound of formula (I) wherein R, $R_1$, $R_2$, $R_3$, $R_4$, $R_5$, n and m are as set forth above, with the proviso that when R is biphenyl-4-yl, $R_1$ is isopropoxy, m and n are both 2, $R_5$ is H, one of $R_2$ or $R_3$ is —CONHOH and the remaining one of $R_2$ or $R_3$ is H, then $R_4$ is not H or benzyloxycarbonyl, and the pharmaceutically acceptable salts thereof.

From all of the above, it can be easily envisaged that the compounds of this invention may have a wide range of applications, in therapy, and may be thus properly formulated according to conventional methods for the intended administration route: i.e. topical, oral and enteral administration.

With the aim of better illustrate the present invention, without posing any limitation to it, the following examples are now given. In this respect, further applications including possible variants to the preparative process, that will become evident to the skilled person, are thus to be considered as comprised within the scope of the present invention.

EXPERIMENTAL SECTION

Some representative compounds of the invention were prepared according to the following Schemes 1 to 6; unless otherwise provided, reference to the compounds numbering as reported in the following schemes will be maintained.

Those presently numbered as compounds (1a-1h) were prepared by the method outlined in Scheme 1.

Optically active α-hydroxy-tert-butyl ester (6) was synthesized by direct esterification of commercially available α-hydroxy acid (5) with N,N-dimethylformamide di-tert-butyl acetal (see Rossello, A. et al.; *Bioorg. Med. Chem. Lett*, 2005, 15, 1321). A Mitsunobu condensation reaction of sulfonamides (7-10) with α-hydroxy-tert-butyl-ester (6), gave tert-butyl esters (11-14). Acid cleavage of esters (11, 14) yielded carboxylic acids (35, 36) which were converted to their O-silylate (37, 38) upon treatment with O-(tert-butyl-dimethylsilyl)hydroxylamine. Hydrolysis with trifluoroacetic acid of tert-butyl O-silylate (37, 38) provided hydroxamic acids (1a, 1h). Tert-butyl esters (17-22) were obtained by Pd-catalyzed hydrogenation of (12, 13) followed by acylation with commercial acyl chlorides. Acid cleavage of esters (17-22) yielded carboxylates (23-28) which were subsequently converted to their respective tert-butyl O-silylate (29, 34). Hydroxamic acids (1b-1g) were then obtained by treatment of (29, 34) with trifluoroacetic acid.

Additional compounds of the invention (2-4) were also prepared according to Scheme 2.

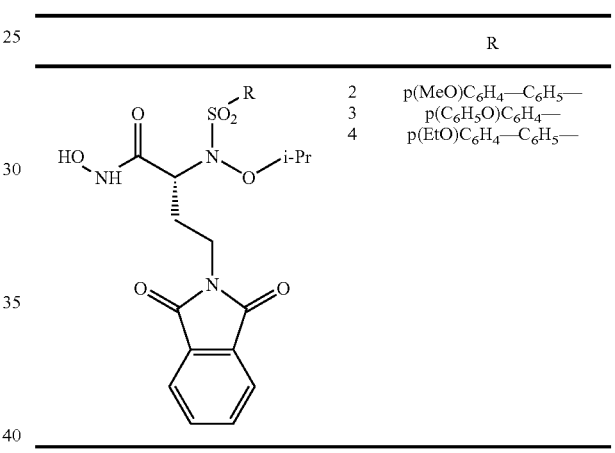

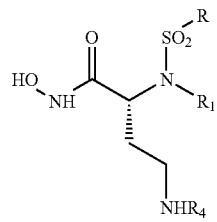

(1a-1h)

| | R | $R_1$ | $R_4$ |
|---|---|---|---|
| 1a | biphenyl-4-yl | benzyloxy | benzyloxycarbonyl |
| 1b | biphenyl-4-yl | isopropoxy | benzoyl |
| 1c | biphenyl-4-yl | isopropoxy | methanesulfonyl |
| 1d | biphenyl-4-yl | isopropoxy | acetyl |
| 1e | biphenyl-4-yl | isopropoxy | phenacetyl |
| 1f | p(MeO)$C_6H_4$—$C_6H_4$— | isopropoxy | acetyl |
| 1g | p(MeO)$C_6H_4$—$C_6H_4$— | isopropoxy | phenacetyl |
| 1h | biphenyl-4-yl | 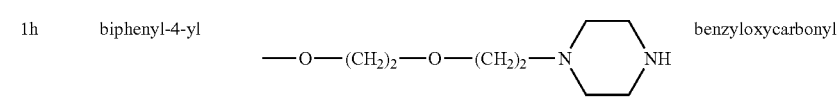 | benzyloxycarbonyl |

(S)-α-Hydroxy-tert-butyl ester (40) was obtained by direct esterification of commercially available α-hydroxy acid (39) using N,N-dimethylformamide di-tert-butyl acetal. A Mitsunobu coupling of sulfonamides (9, 41, and 42) with α-hydroxy-tert-butyl-ester (40), gave tert-butyl esters (43-45). Acid cleavage of (43, 44) yielded carboxylic acids (46, 47) which were converted to their O-silylate (48, 49) upon treatment with O-(tert-butyl-dimethylsilyl)hydroxylamine. Hydrolysis with trifluoroacetic acid of tert-butyl O-silylate (48, 49) provided hydroxamic acids (2 and 3). Suzuki coupling of commercially available 4-ethoxyphenyl boronic acid with ester (45) gave biphenyl ester (50), which was converted to hydroxamic acid (4) using the procedure described above.

An additional compound of the invention, presently indicated as compound (64), wherein both $R_2$ and $R_3$, in formula (I) are H atoms, was prepared as per Scheme 5 below, through Mitsunobu condensation reaction between commercially available alcohol (63) with sulphonamide (8)

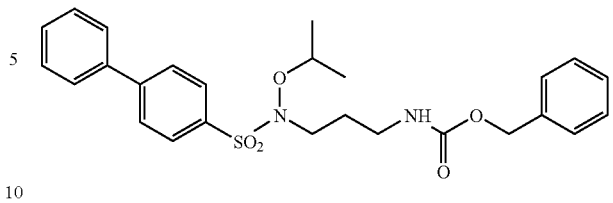

(64)

Sulfonamides (7-10 and 41, 42) used in Schemes 1 and 2 were prepared as shown in Scheme 3. Commercially available arylsulfonyl chlorides (56-59) were coupled with the appropriate O-alkylhydroxylamines (53-55) upon treatment with N-methylmorpholine (see Rossello, A. et al.; *Bioorg. Med. Chem.* 2004, 12, 2441). While O-alkylhydroxylamines (53 and 54) were commercially available, (55) was prepared as described in Scheme 4. N-protection of commercial amino alcohol (60) upon reaction with di-tert-butyldicarbonate gave piperazine derivative (61). Mitsunobu reaction with N-hydroxyphthalimide provided (62) which was converted to (55) by hydrazinolysis with hydrazine hydrate in ethanol.

Additional compounds of the invention (1i-1k) having the following formulae were also prepared:

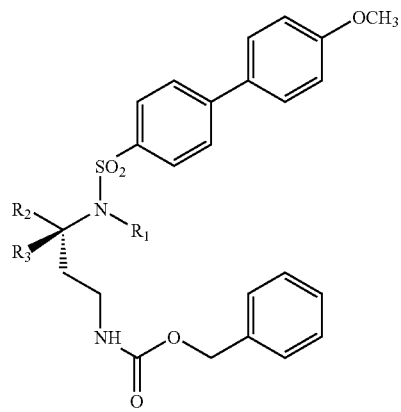

(1i-1k)

One of $R_2$ or $R_3$ is H
and the other of $R_2$ or $R_3$ is:                                             $R_1$

| | | |
|---|---|---|
| 1i | —COOH | 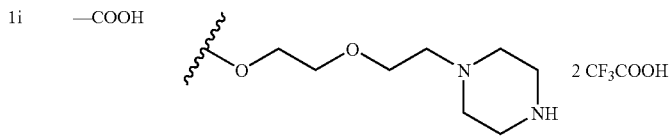 2 CF$_3$COOH |
| 1j | —CONHOH | 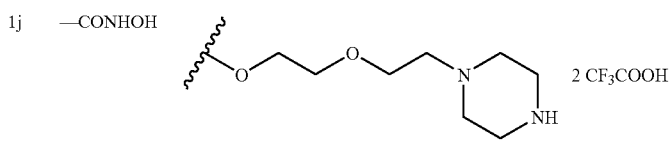 2 CF$_3$COOH |
| 1k | —CONHOH | 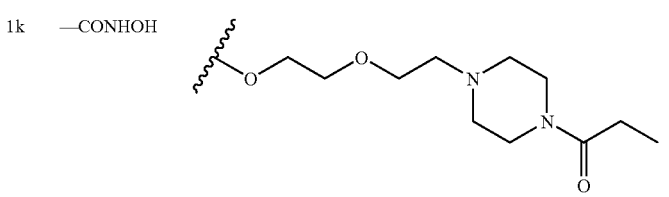 |

Compounds (1i) and (1j) were prepared as shown in scheme 6 by properly reacting, as formerly reported under Mitsunobu coupling conditions, the sulphonamido derivative (65) with compound (6) of scheme 1. The obtained compound (66) was then deprotected with trifluoroacetic acid so as to obtain compound (1i) as di-trifluoroacetate salt.

This latter carboxylic acid was then converted into the corresponding hydroxamic acid derivative (1j) di-trifluoroacetate, as formerly reported.

Compound (1j) was then acylated at the piperazino N atom with 2,5-dioxipyrrolidine-1-yl propionate, by working according to conventional methods in the presence of triethylamine, so as to obtain the corresponding compound (1k).

The starting material (65) was obtained, by analogy, as reported in schemes 3 and 4 for the preparation of compound (10).

1H-NMR spectra were recorded on a Varian Gemini 200 (200 MHz) using $CDCl_3$ or $DMSO-d_6$, as solvents.

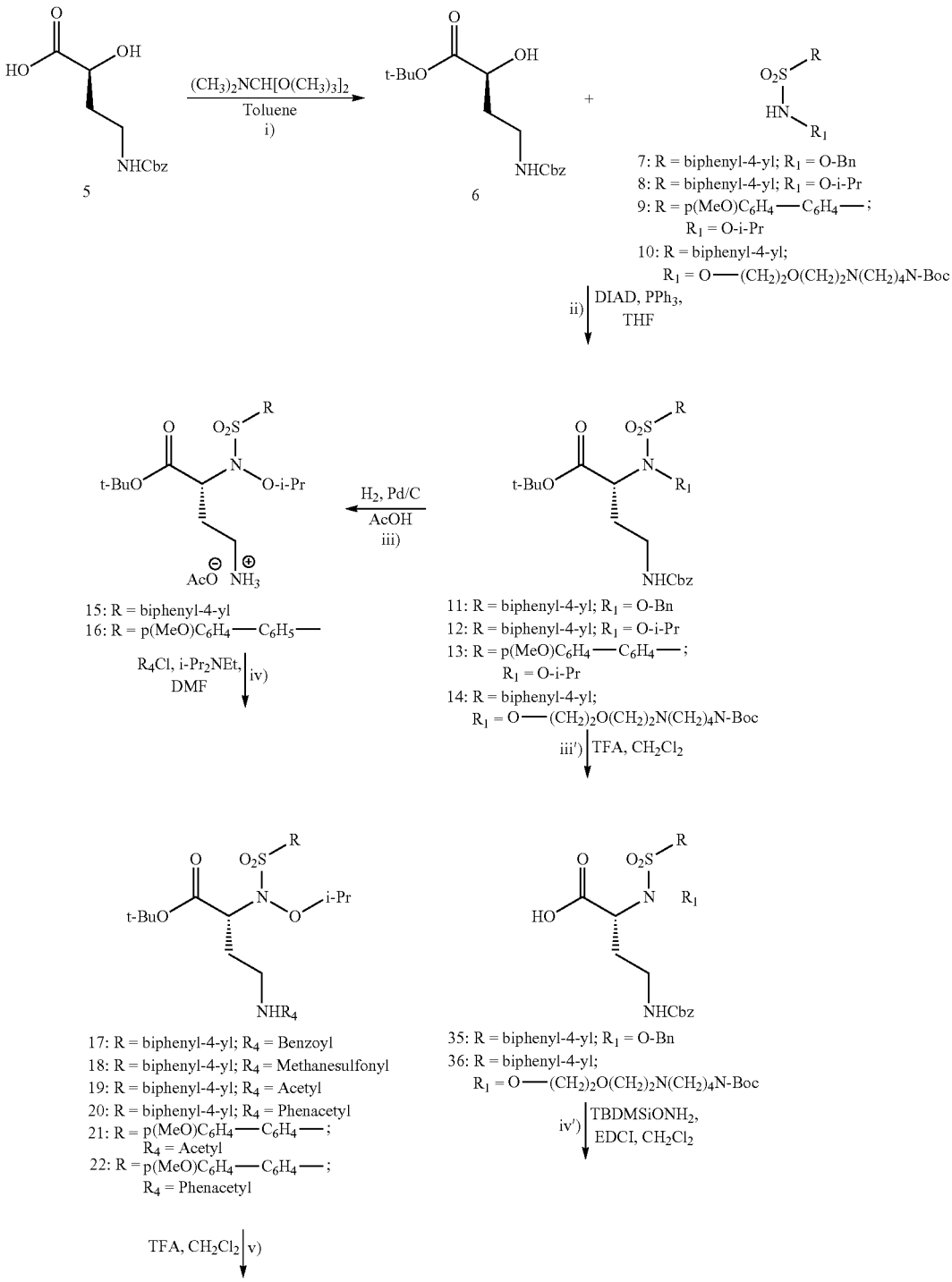

Scheme 1

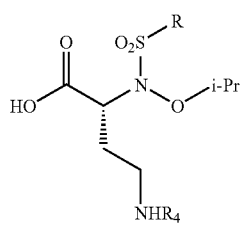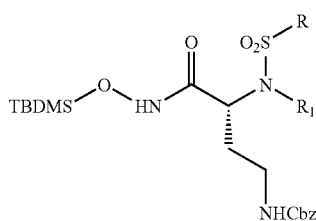

23: R = biphenyl-4-yl; R$_4$ = Benzoyl
24: R = biphenyl-4-yl; R$_4$ = Methanesulfonyl
25: R = biphenyl-4-yl; R$_4$ = Acetyl
26: R = biphenyl-4-yl; R$_4$ = Phenacetyl
27: R = p(MeO)C$_6$H$_4$—C$_6$H$_4$—;
    R$_4$ = Acetyl
28: R = p(MeO)C$_6$H$_4$—C$_6$H$_4$—;
    R$_4$ = Phenacetyl 37: R = biphenyl-4-yl; R$_1$ = O-Bn
38: R = biphenyl-4-yl;
    R$_1$ = O—(CH$_2$)$_2$O(CH$_2$)$_2$N(CH$_2$)$_4$N-Boc TBDMSiONH$_2$, EDCI, CH$_2$Cl$_2$ | vi)

v') | TFA, CH$_2$Cl$_2$

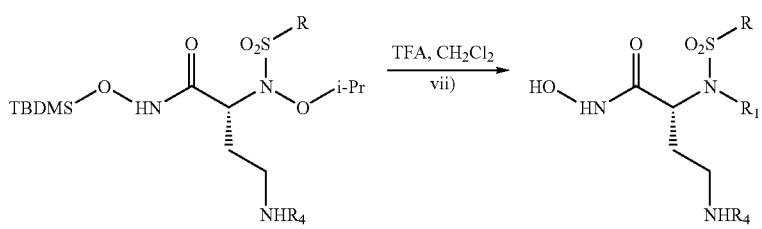

29: R = biphenyl-4-yl; R$_4$ = Benzoyl
30: R = biphenyl-4-yl; R$_4$ = Methanesulfonyl
31: R = biphenyl-4-yl; R$_4$ = Acetyl
32: R = biphenyl-4-yl; R$_4$ = Phenacetyl
33: R = p(MeO)C$_6$H$_4$—C$_6$H$_4$—;
    R$_4$ = Acetyl
34: R = p(MeO)C$_6$H$_4$—C$_6$H$_4$—;
    R$_4$ = Phenacetyl TFA, CH$_2$Cl$_2$
vii)

(1a-h)

Scheme 2

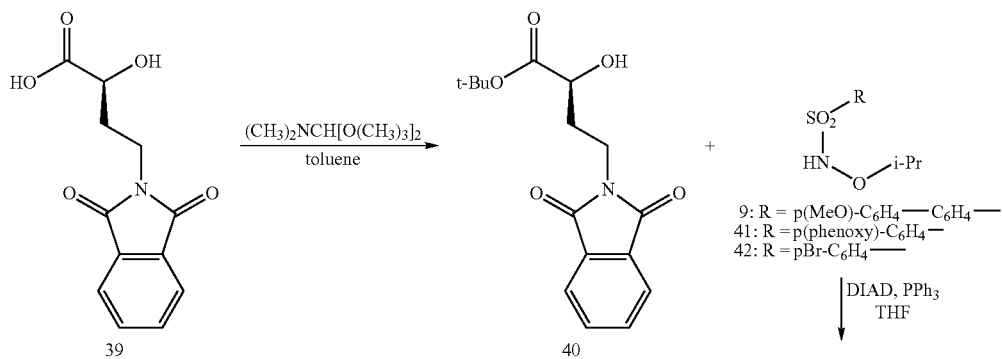

9: R = p(MeO)-C$_6$H$_4$—C$_6$H$_4$—
41: R = p(phenoxy)-C$_6$H$_4$—
42: R = pBr-C$_6$H$_4$—

DIAD, PPh$_3$
THF

-continued
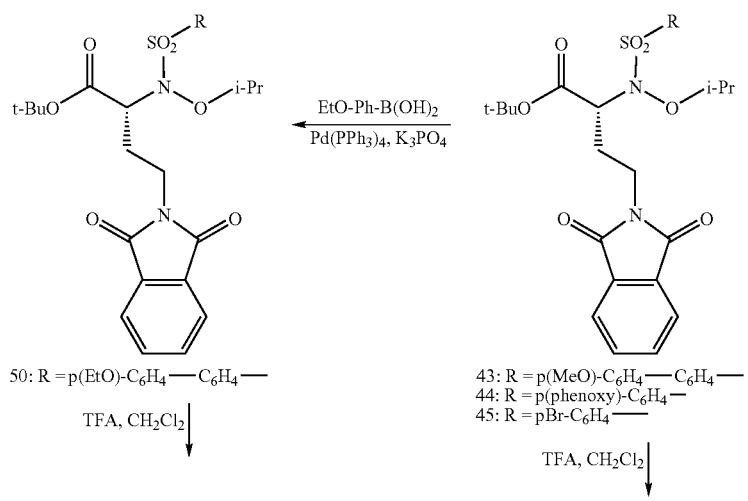
50: R = p(EtO)-C₆H₄ — C₆H₄ —
43: R = p(MeO)-C₆H₄ — C₆H₄ —
44: R = p(phenoxy)-C₆H₄ — C₆H₄ —
45: R = pBr-C₆H₄ —
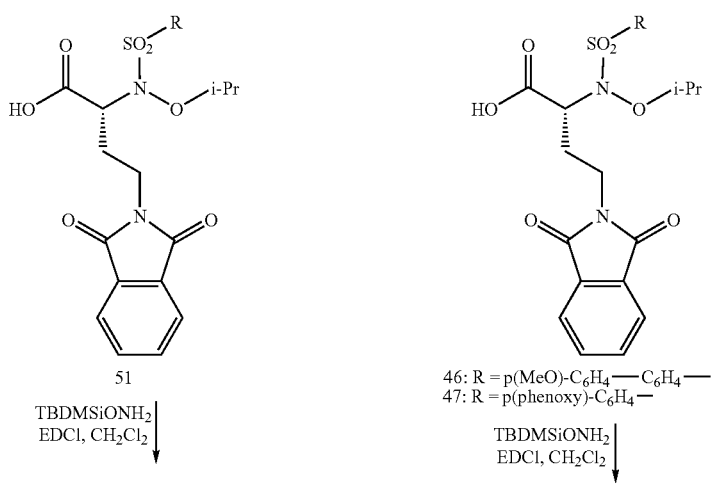
51
46: R = p(MeO)-C₆H₄ — C₆H₄ —
47: R = p(phenoxy)-C₆H₄ —
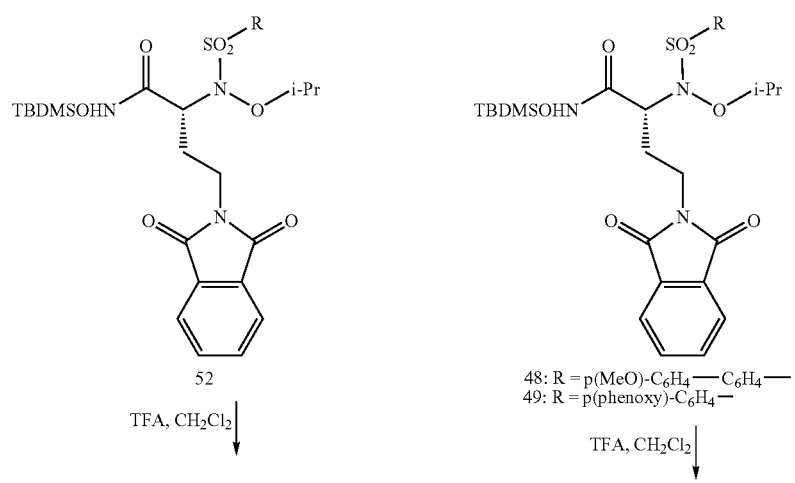
52
48: R = p(MeO)-C₆H₄ — C₆H₄ —
49: R = p(phenoxy)-C₆H₄ —

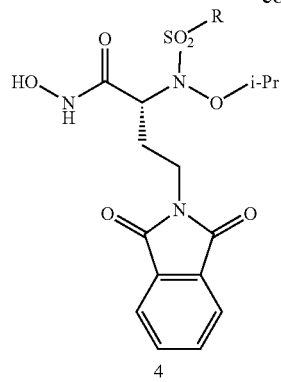

4

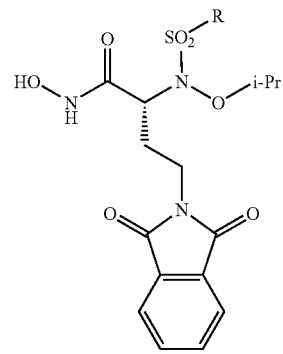

2: R = p(MeO)-C$_6$H$_4$—C$_6$H$_4$—
3: R = p(phenoxy)-C$_6$H$_4$—

Scheme 3

R$_1$—NH$_2$
53: R$_1$ = benzyloxy
54: R$_1$ = isopropoxy
55: —O—(CH$_2$)$_2$—O—(CH$_2$)$_2$—N[(CH$_2$)$_4$N-Boc

+

R—SO$_2$Cl    $\xrightarrow{\text{NMM, THF}}$
56: R = biphenyl-4-yl
57: R = p(MeO)-C$_6$H$_4$—C$_6$H$_4$—
58: R = p(PhO)-C$_6$H$_4$—
59: R = pBr-C$_6$H$_4$—

-continued

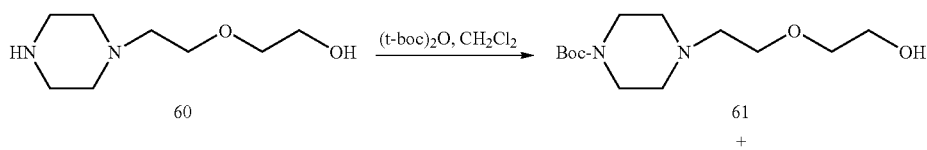

7: R = biphenyl-4-yl; R$_1$ = benzyloxy
8: R = biphenyl-4-yl; R$_1$ = isopropoxy
9: R = p(MeO)-C$_6$H$_4$—C$_6$H$_4$—; R$_1$ = isopropoxy
10: R = biphenyl-4-yl; R$_1$ = —O—(CH$_2$)$_2$O(CH$_2$)$_2$N[(CH$_2$)$_4$]N-Boc
41: R = p(PhO)-C$_6$H$_4$—; R$_1$ = isopropoxy
42: R = pBr-C$_6$H$_4$—; R$_1$ = isopropoxy Scheme 4

+

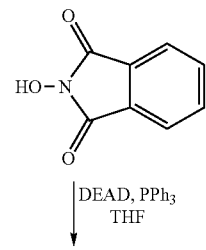

$\downarrow$ DEAD, PPh$_3$ THF

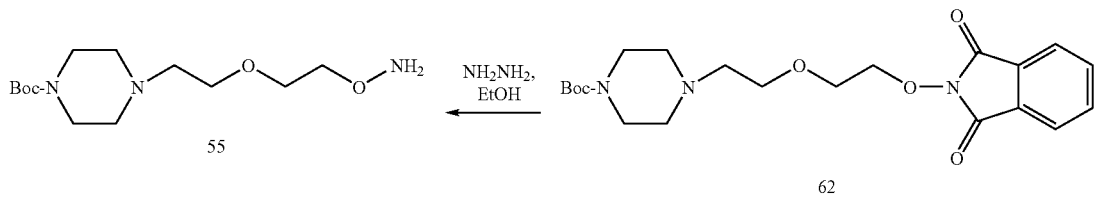

Scheme 5
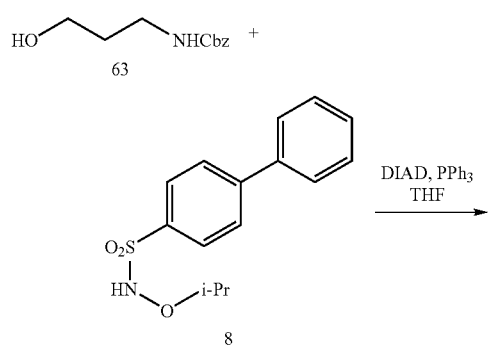
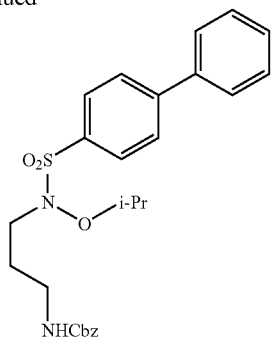
Scheme 6
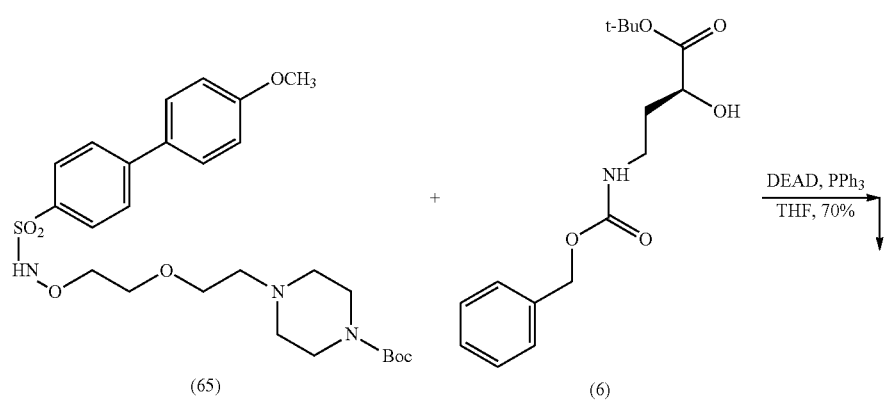
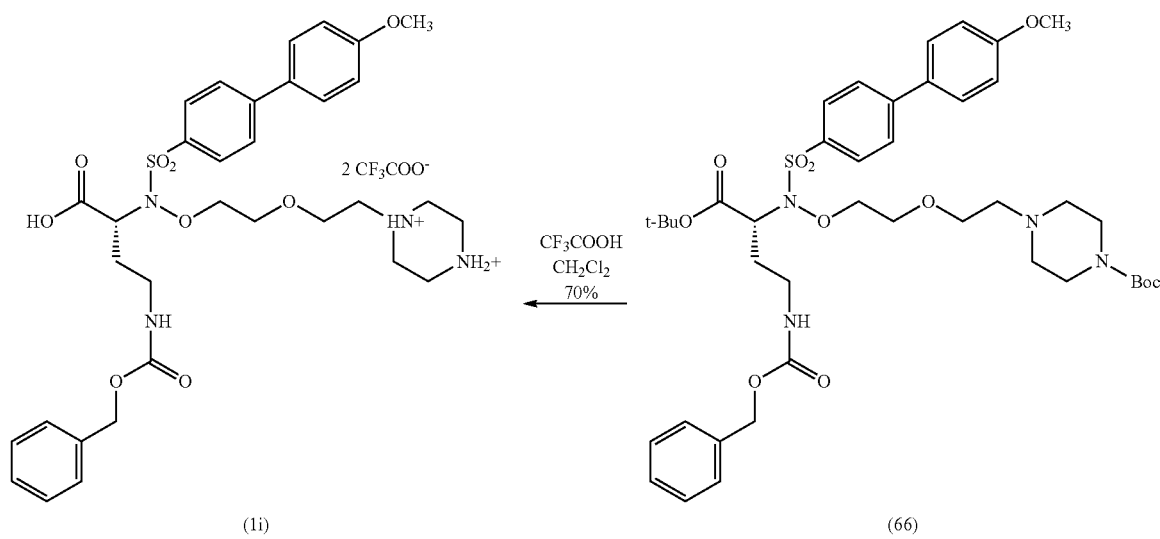

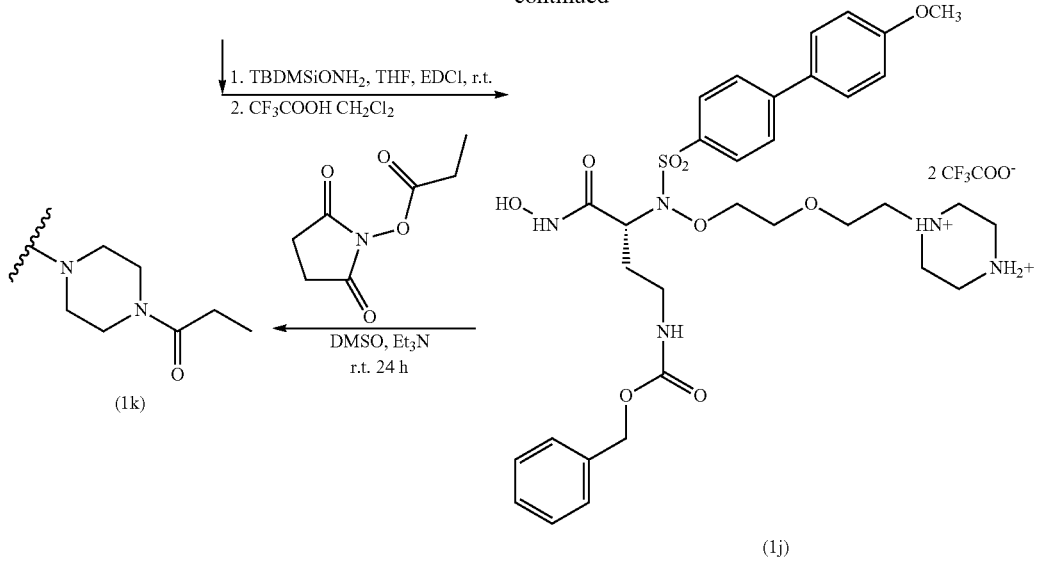

Example 1

Preparation of compound (1a): (R)-benzyl 3-(N-(benzyloxy)biphenyl-4-ylsulfonamido)-4-(hydroxyamino)-4-oxobutylcarbamate Preparation of Compound (6)

A solution of (S)-(+)-Z-4-amino-2-hydroxybutyric acid (5) (5 g, 19.74 mmol) in toluene (38 mL) containing N,N-dimethylformamide di-tert-butyl acetal (18.92 mL, 78.96 mmol) was heated to 95° C. for 3 h. The solvent was then evaporated and the crude product was purified by flash chromatography on silica gel (n-hexane/EtOAc=7:4) to give (6) (3.4 g, 55.7% yields) as yellow solid.

Mp 42-44° C.; $[\alpha]^{20}_D = -5.9°$ (c=10.1 mg/ml, CHCl$_3$)

$^1$H-NMR (CDCl$_3$) δ: 1.47 (s, 9H); 1.76-1.85 (m, 1H); 1.94-2.09 (m, 1H); 2.74 (br s, 1H); 3.36 (dd, J=6.04 Hz, J=11.99 Hz, 2H); 4.10 (dd, J=4.02 Hz, J=8.05 Hz, 1H); 5.09 (s, 2H); 5.21 (br s, 1H); 7.31-7.37 (m, 5H)

Anal. Calcd. for C$_{16}$H$_{23}$NO$_5$: C, 62.12; H, 7.49; N, 4.53. Found: C, 62.22; H, 7.48; N, 4.53.

Preparation of Compound (7)

A solution of biphenyl-4-sulfonyl chloride (56) (3.17 g, 12.53 mmol) in anhydrous THF (32 mL) was added dropwise to a stirred and cooled (0° C.) solution of O-benzylhydroxylamine hydrochloride (53) (2 g, 12.53 mmol) and N-methylmorpholine (2.75 mL, 25.06 mmol) in anhydrous THF (32 mL). After 30 min. under these conditions, the reaction mixture was stirred at rt for 3 days, then was diluted with AcOEt and washed with H$_2$O giving, after work-up, sulfonamide (7) (3.62 g, 85%) as a white solid.

Mp=130-132° C.;

$^1$H-NMR (CDCl$_3$) δ: 5.01 (s, 2H); 7.01 (s, 1H); 7.35 (m, 5H); 7.44-7.51 (m, 3H); 7.57-7.62 (m, 2H); 7.70-7.75 (m, 2H); 7.97-8.01 (m, 2H).

Preparation of Compound (11)

Diisopropyl azodicarboxylate (DIAD) (1.28 mL, 6.52 mmol) was added dropwise to a solution containing the secondary alcohol (6) (0.8 g, 2.61 mmol), the sulfonamide (7) (1.3 g, 3.91 mmol) and triphenylphosphine (2.05 g, 7.83 mmol) in anhydrous THF (45 mL) under nitrogen atmosphere at 0° C. The resulting solution was stirred for 5 h at rt and evaporated under reduced pressure to afford a crude product, which was purified by flash chromatography on silica gel (n-hexane/EtOAc=3:1) to yield compound (11) (0.95 g, 58% yield) as pure yellow oil.

$^1$H-NMR (CDCl$_3$) δ: 1.25 (s, 9H); 1.90-2.04 (m, 2H); 3.16-3.40 (m, 2H); 4.16 (t, J=7.1 Hz, 1H); 4.93-5.00 (m, 1H); 5.07-5.19 (m, 4H); 7.33-7.37 (m, 10H); 7.41-7.59 (m, 5H); 7.66-7.70 (m, 2H); 7.92-7.97 (m, 2H).

$^{13}$C-NMR (CDCl$_3$) δ: 22.09; 27.87; 37.59; 62.75; 66.76; 80.87; 82.56; 127.43; 127.67; 128.16; 128.56; 128.72; 128.92; 129.14; 129.89; 129.94; 133.89; 134; 80; 139.17; 146.84; 156.27.

Preparation of Compound (35)

Trifluoroacetic acid (0.9 mL, 57.00 mmol) was added dropwise to a stirred solution of tert-butyl ester (11) (136 mg, 0.21 mmol) in freshly distilled CH$_2$Cl$_2$ (1.0 mL), cooled to 0° C. The solution was stirred for 5 h at 0° C. and the solvent was removed in vacuo to give compound (35) (128 mg, 100% yield) as oil.

$^1$H-NMR (CDCl$_3$) δ: 1.60-1.70 (m, 1H); 1.88-2.08 (m, 1H); 3.19 (m, 2H); 4.30 (t, J=6.9 Hz, 1H); 5.02-5.17 (m, 4H); 7.28-7.34 (m, 10H); 7.40-7.51 (m, 3H); 7.55-7.59 (m, 2H); 7.65-7.70 (m, 2H); 7.91-7.95 (m, 2H).

Preparation of Compound (37)

To a solution of carboxylic acid (35) (117 mg, 0.2 mmol) and O-(tert-butyldimethyl-silyl)hydroxylamine (44 mg, 0.3 mmol) in freshly distilled CH$_2$Cl$_2$ (3.6 mL) cooled to 0° C., was added 1-[3-(dimethylamino)propyl]-3-ethyl carbodiimide hydrochloride (EDCI) portionwise (57.5 mg, 0.3 mmol). After stirring at rt for 20 h, the mixture was washed with H$_2$O and the organic phase was dried and evaporated in vacuo. The residue was purified by flash chromatography on silica gel (n-hexane/EtOAc=2.5:1) to yield compound (37) (28 mg, 20% yield) as yellow oil.

$^1$H-NMR (CDCl$_3$) δ: 0.13 (s, 6H); 0.90 (s, 9H); 1.90-2.11 (m, 2H); 2.80-3.40 (m, 2H); 4.13-4.22 (m, 1H); 5.02-5.27 (m, 4H); 7.31-7.46 (m, 13H); 7.53-7.58 (m, 2H); 7.64-7.68 (m, 2H); 7.84-7.88 (m, 2H).

Preparation of the Title Compound (1a)

Trifluoroacetic acid (0.15 mL, 1.85 mmol) was added dropwise to a stirred solution of compound (37) (23 mg, 0.03 mmol) in freshly distilled CH$_2$Cl$_2$ (1 mL), cooled to 0° C. The solution was stirred for 5 h at 0° C. and the solvent was removed in vacuo to give a crude product that was recrystallized from Et$_2$O and n-hexane to give (1a) (10 mg, 53% yield) as solid.

$^1$H-NMR (CDCl$_3$) δ: 1.99 (m, 2H); 3.00-3.35 (m, 2H); 4.29 (m, 1H); 5.08-5.26 (m, 4H); 7.34-7.45 (m, 13H); 7.53-7.58 (m, 2H); 7.66-7.70 (m, 2H); 7.87-7.91 (m, 2H).

Example 2

Preparation of compound (1b): (R)—N-(4-(hydroxyamino)-3-(N-isopropoxybiphenyl-4-ylsulfonamido)-4-oxobutyl)benzamide Preparation of Compound (8)

N-isopropoxy-1,1'-biphenyl-4-sulfonamide was prepared as previously described by Rossello, A. et al. (*Bioorg. Med. Chem.* 2004, 12, 2441).

Preparation of Compound (12)

Tert-butyl ester (12) was prepared from sulfonamide derivative (8) (1.08 g, 3.72 mmol) and alcohol (6) (0.76 g, 2.48 mmol) following the procedure previously described for the preparation of compound (11), as set forth in Example 1. The crude reaction mixture was purified by flash chromatography (n-hexane/AcOEt=5:1), to give (12) (1.14 g, 79% yield) as a yellow oil.

$[α]^{20}{}_D$=+55° (c=9.1 mg/L, CHCl$_3$);

$^1$H-NMR (CDCl$_3$) δ: 1.22-1.25 (m, 15H); 2.04 (m, 2H); 3.22-3.37 (m, 2H); 4.12 (dd, J=7.14 Hz, J=14.29 Hz, 1H); 4.43 (septet, J=6.2 Hz, 1H); 5.08 (s, 2H); 7.34 (m, 5H); 7.42-7.53 (m, 3H); 7.55-7.61 (m, 2H); 7.7-7.74 (m, 2H); 7.94-7.98 (m, 2H).

Preparation of Compound (15)

A solution of compound (12) (0.74 g, 1.27 mmol) in MeOH (80 mL) was stirred under hydrogen atmosphere in the presence of 10% Pd—C (0.20 g) and glacial acetic acid (80 mL) for 17 h at room temperature. The resulting mixture was filtered on celite and the filtrate was evaporated under reduced pressure to give (15) (0.60 g, 93% yield) as a brownish oil.

$^1$H-NMR (CDCl3) δ: 1.10 (brs, 9H); 1.20 (t, J=4.4 Hz, 6H); 2.16-2.30 (m, 2H); 3.16 (m, 2H); 4.34-4.46 (m, 2H); 7.40-7.51 (m, 3H); 7.56-7.59 (m, 2H); 7.71-7.75 (m, 2H); 8.00-8.04 (m, 2H).

$^{13}$C-NMR (CDCl3) δ: 21.15; 21.22; 27.72; 36.70; 62.97; 80.03; 82.49; 127.03; 127.45; 127.59; 127.76; 128.67; 129.14; 130.49; 133.60; 139.30; 146.89.

Preparation of Compound (17)

A solution of compound (15) (0.30 g, 0.59 mmol) in dry DMF (6 mL) was treated with benzoyl chloride (0.08 mL, 0.70 mmol) and i-Pr$_2$NEt (0.20 mL, 1.18 mmol). The reaction mixture was stirred at rt for 17 h, then was diluted with ethyl acetate, washed with H$_2$O, dried over Na$_2$SO$_4$ and evaporated. The crude was purified by flash chromatography (n-hexane/AcOEt=2.5:1), to give (17) (112 mg, 34% yield) as a yellow oil.

$^1$H-NMR (CDCl$_3$) δ: 1.13 (brs, 9H); 1.23 (d, J=5.1 Hz, 3H); 1.26 (d, J=4.4 Hz, 3H); 2.10-2.21 (m, 2H); 3.34-3.50 (m, 1H); 3.80-3.92 (m, 1H); 4.23 (t, J=7.1 Hz, 1H); 4.45 (septet, 1H); 7.39-7.59 (m, 10H); 7.69-7.73 (m, 2H); 7.93-7.98 (m, 2H).

Preparation of Compound (23)

Carboxylic acid (23) (89 mg, 100% yield) was prepared from ester derivative (17) (0.10 g, 0.18 mmol) following the procedure previously described for the preparation of compound (35), as per Example 1.

$^1$H-NMR (CDCl$_3$) δ: 1.20 (t, J=5.1 Hz, 6H); 1.80-2.28 (m, 2H); 3.40-3.55 (m, 1H); 3.60-3.82 (m, 1H); 4.30-4.50 (m, 2H); 6.56 (brs, 1H); 7.43-7.58 (m, 10H); 7.66-7.69 (m, 2H); 7.91-7.94 (m, 2H).

Preparation of Compound (29)

Following an analogous procedure to that used for the preparation of compound (37), in Example 1, carboxylic acid (23) (90 mg, 0.18 mmol) was coupled with O-(tert-butyldimethyl-silyl)hydroxylamine. Silica gel column chromatography (n-hexane/AcOEt=2:1) yielded the desired product (30 mg, 27% yield).

$^1$H-NMR (CDCl$_3$) δ: 0.16 (s, 6H); 0.93 (s, 9H); 1.22 (d, J=6.2 Hz, 3H); 1.28 (d, J=6.2 Hz, 3H); 2.02-2.16 (m, 2H); 3.20 (m, 1H); 3.43 (m, 1H); 4.06-4.20 (m, 1H); 4.46 (septet, 1H); 6.76 (brs, 1H); 7.35-7.65 (m, 10H); 7.73-7.77 (m, 2H); 7.87-7.91 (m, 2H); 9.01 (brs, 1H).

Preparation of the Title Compound (1b)

Following a procedure analogous to that used for the preparation of compound (1a), in Example 1, tert-butyl O-silylate (29) (30 mg, 0.05 mmol) was treated with TFA to give the desired hydroxamic acid (15 mg, 60.5% yield) after recrystallization from Et$_2$O.

$^1$H-NMR (CDCl$_3$) δ: 1.24 (t, J=6.5 Hz, 6H); 1.44-1.69 (m, 1H); 2.05-2.21 (m, 1H); 3.10-3.50 (m, 2H); 4.20-4.50 (m, 2H); 7.10 (brs, 1H); 7.30-7.55 (m, 10H); 7.59-7.63 (m, 2H); 7.86-7.90 (m, 2H).

Example 3

Preparation of Compound (1c): (R)—N-hydroxy-2-(N-isopropoxybiphenyl-4-ylsulfonamido)-4-(methylsulfonamido)butanamide Preparation of Compound (18)

A solution of compound (15) prepared according to Example 2 (0.30 g, 0.60 mmol), in dry THF (3 mL), was treated with methanesulfonyl chloride (0.05 mL, 0.60 mmol) and N-methylmorpholine (0.13 mL, 1.2 mmol). The reaction mixture was stirred at room temperature overnight, then was diluted with AcOEt, washed with H$_2$O, dried over Na$_2$SO$_4$ and evaporated. The crude was purified by flash chromatography (n-hexane/AcOEt=3:2), to give (18) (100 mg, 32% yield) as a yellow oil.

$^1$H-NMR (CDCl$_3$) δ: 1.14 (brs, 9H); 1.20-1.26 (m, 6H); 2.04 (brs, 2H); 2.95 (s, 3H); 3.29 (brs, 2H); 4.25 (t, J=7.1 Hz, 1H); 4.42 (septet, 1H); 7.43-7.54 (m, 3H); 7.58-7.62 (m, 2H); 7.74-7.78 (m, 2H); 7.96-8.00 (m, 2H).

Preparation of Compound (24)

Following a procedure analogous to that used for the preparation of compound (35), in Example 1, ester derivative (18) (100 mg, 0.19 mmol) was treated with TFA to give the desired carboxylic acid (24) (73 mg, 79% yield), after recrystallization from Et$_2$O and n-hexane.

$^1$H-NMR (CDCl$_3$) δ: 1.22 (d, J=6.2 Hz, 6H); 2.06-2.17 (m, 2H); 2.91 (s, 3H); 3.21 (brs, 2H); 4.34-4.44 (m, 2H); 7.42-7.53 (m, 3H); 7.61-7.66 (m, 2H); 7.74-7.78 (m, 2H); 7.95-7.99 (m, 2H).

Preparation of Compound (30)

Following a procedure analogous to that used for the preparation of compound (37), in Example 1, carboxylic acid (24) (70 mg, 0.15 mmol) was coupled with O-(tert-butyldimethylsilyl)hydroxylamine. Silica gel column chromatography (n-hexane/AcOEt=1:1) yielded the desired product (32 mg, 33% yield).

$^1$H-NMR (CDCl$_3$) δ: 0.15 (s, 6H); 0.93 (s, 9H); 1.20 (d, J=6.2 Hz, 3H); 1.25 (d, J=5.8 Hz, 3H); 2.00-2.15 (m, 2H); 2.83 (s, 3H); 2.89-2.99 (m, 2H); 4.23-4.29 (m, 1H); 4.40 (septet, 1H); 7.42-7.52 (m, 3H); 7.61-7.66 (m, 2H); 7.79-7.83 (m, 2H); 7.96-8.00 (m, 2H); 8.64 (brs, 1H).

Preparation of the Title Compound (1c)

Following a procedure analogous to that used for the preparation of the compound (1a), in Example 1, tert-butyl O-silylate (30) (30 mg, 0.05 mmol) was treated with TFA to give the desired hydroxamic acid (15 mg, 60% yield), after recrystallization from Et$_2$O and n-hexane.

$^1$H-NMR (CDCl$_3$) δ: 1.24 (t, J=6.4 Hz, 6H); 2.01-2.18 (m, 2H); 2.88 (s, 3H); 3.00-3.20 (m, 2H); 4.40-4.48 (m, 2H); 4.88 (brs, 1H); 7.42-7.53 (m, 3H); 7.62-7.66 (m, 2H); 7.78-7.83 (m, 2H); 7.95-7.99 (m, 2H).

Example 4

Preparation of Compound (1d): (R)-4-acetamido-N-hydroxy-2-(N-isopropoxybiphenyl-4-ylsulfonamido)butanamide Preparation of Compound (19)

Following a procedure analogous to that used for the preparation of compound (17), in Example 2, ester derivative (15) (0.30 g, 0.59 mmol) was acylated with acetyl chloride. Silica gel column chromatography (n-hexane/AcOEt=1:1) yielded the desired product (19) (60 mg, 22% yield).

$^1$H-NMR (CDCl$_3$) δ: 1.19-1.24 (m, 15H); 1.90-2.01 (m, 5H); 3.13-3.23 (m, 1H); 3.53 (m, 1H); 4.12 (m, 1H); 4.40 (septet, 1H); 6.11 (brs, 1H); 7.41-7.52 (m, 3H); 7.57-7.61 (m, 2H); 7.72-7.76 (m, 2H); 7.94-7.98 (m, 2H).

$^{13}$C-NMR (CDCl$_3$) δ: 21.17; 23.48; 27.76; 36.17; 63.59; 79.80; 82.25; 127.39; 127.52; 128.72; 129.16; 130.14; 133.80; 139.19; 146.84; 170.22.

Preparation of Compound (25)

Following a procedure analogous to that used for the preparation of compound (35), in Example 1, ester derivative (19) (60 mg, 0.12 mmol) was treated with TFA to give the desired carboxylic acid (25) (60 mg, 100% yield).

$^1$H-NMR (CDCl$_3$) δ: 1.16 (d, J=2.01, 3H); 1.19 (d, J=2.01, 3H); 1.92-2.10 (m, 5H); 3.15-3.60 (m, 2H); 4.20-4.39 (m, 2H); 6.73 (brs, 1H); 7.42-7.52 (m, 3H); 7.59-7.63 (m, 2H); 7.73-7.77 (m, 2H); 7.93-7.97 (m, 2H); 10.24 (brs, 1H).

Preparation of Compound (31)

Following a procedure analogous to that used for the preparation of compound (37), in Example 1, carboxylic acid (25) (60 mg, 0.14 mmol) was coupled with O-(tert-butyldimethylsilyl)hydroxylamine. Silica gel column chromatography (n-hexane/AcOEt=1:2) yielded the desired product (12 mg, 16% yield).

$^1$H-NMR (CDCl$_3$) δ: 0.15 (s, 6H); 0.93 (s, 9H); 1.21 (d, J=6.2 Hz, 3H); 1.25 (d, J=6.2 Hz, 3H); 1.90-2.05 (m, 5H); 2.80-3.26 (m, 2H); 4.06-4.16 (m, 1H); 4.44 (septet, 1H); 5.95 (brs, 1H); 7.42-7.53 (m, 3H); 7.58-7.65 (m, 2H); 7.76-7.80 (m, 2H); 7.92-7.96 (m, 2H); 8.90 (brs, 1H).

Preparation of the Title Compound (1d)

Following a procedure analogous to that used for the preparation of compound (1a), in Example 1, tert-butyl O-silylate (31) (12 mg, 0.02 mmol) was treated with TFA to give the desired hydroxamic acid (11 mg, 90% yield).

$^1$H-NMR (CDCl$_3$) δ: 1.23 (d, J=6.7, 6H); 1.90-2.08 (m, 5H); 3.04-3.35 (m, 2H); 4.22 (m, 1H); 4.40 (septet, 1H); 6.73 (brs, 1H); 7.42-7.52 (m, 3H); 7.59-7.63 (m, 2H); 7.76-7.80 (m, 2H); 7.92-7.96 (m, 2H).

Example 5

Preparation of Compound (1e): (R)—N-hydroxy-2-(N-isopropoxybiphenyl-4-ylsulfonamido)-4-(2-phenylacetamido)butanamide Preparation of Compound (20)

Following a procedure analogous to that used for the preparation of compound (17), in Example 2, ester derivative (15) (0.30 g, 0.59 mmol) was acylated with phenylacetyl chloride. Silica gel column chromatography (n-hexane/AcOEt=2:1) yielded the desired product (55 mg, 16% yield).

$^1$H-NMR (CDCl$_3$) δ: 1.10-1.22 (m, 15H); 1.81-2.05 (m, 2H); 3.00-3.21 (m, 1H); 3.50-3.60 (m, 3H); 3.96 (t, J=7.5 Hz, 1H); 4.38 (septet, 1H); 7.28-7.37 (m, 5H); 7.43-7.54 (m, 3H); 7.57-7.62 (m, 2H); 7.68-7.73 (m, 2H); 7.80-7.84 (m, 2H).

Preparation of Compound (26)

Following a procedure analogous to that used for the preparation of compound (35), in Example 1, ester derivative (20) (55 mg, 0.09 mmol) was treated with TFA to give the desired carboxylic acid (26) (53 mg, 100% yield).

$^1$H-NMR (CDCl$_3$) δ: 1.14 (d, J=3.4, 3H); 1.17 (d, J=3.4, 3H); 1.93-2.10 (m, 2H); 3.14 (m, 1H); 3.47 (m, 1H); 3.61 (s, 2H); 4.13 (t, J=7.3 Hz, 1H); 4.33 (septet, 1H); 5.32 (brs, 1H); 6.14 (brs, 1H); 7.22-7.26 (m, 1H); 7.30-7.37 (m, 4H); 7.42-7.53 (m, 3H); 7.58-7.63 (m, 2H); 7.67-7.73 (m, 2H); 7.82-7.86 (m, 2H).

Preparation of Compound (32)

Following a procedure analogous to that used for the preparation of compound (37), in Example 1, carboxylic acid (26) (53 mg, 0.10 mmol) was coupled with O-(tert-butyldimethylsilyl)hydroxylamine to give compound (32) (54 mg, 80% yield).

Preparation of the Title Compound (1e)

Following a procedure analogous to that used for the preparation of compound (1a), in Example 1, tert-butyl O-silylate (32) (54 mg, 0.08 mmol) was treated with TFA to give the desired hydroxamic acid (30 mg, 68% yield), after recrystallization from Et$_2$O and n-hexane.

$^1$H-NMR (CDCl$_3$) δ: 1.18-1.32 (m, 6H); 1.83-2.22 (m, 2H); 3.10-3.28 (m, 2H); 3.48 (s, 2H); 4.11 (m, 1H); 4.39 (septet, 1H); 6.23 (brs, 1H); 7.16-7.36 (m, 5H); 7.43-7.47 (m, 3H); 7.57-7.61 (m, 2H); 7.67-7.72 (m, 2H); 7.86-7.90 (m, 2H).

Example 6

Preparation of Compound (1f): (R)-4-acetamido-N-hydroxy-2-(N-isopropoxy-4'-methoxybiphenyl-4-ylsulfonamido)butanamide Preparation of Compound (9)

A solution of the commercially available 4'-methoxy-biphenyl-4-yl sulfonyl chloride (1 g, 3.53 mmol) in anhydrous THF (8 mL) was added dropwise to a stirred and cooled (0° C.) solution of O-isopropylhydroxylamine hydrochloride (0.4 g, 3.53 mmol) and N-methylmorpholine (0.77 mL, 7.06 mmol) in anhydrous THF (8 mL). After 30 min under these conditions, the reaction mixture was stirred at room temperature for 3 days, then was diluted with AcOEt and washed with H$_2$O giving, after work-up, sulfonamide (9) (0.94 g, 83% yield) as a white solid.

Mp=162-163° C.;

$^1$H-NMR (CDCl$_3$) δ: 1.20 (d, J=6.2 Hz, 6H); 3.86 (s, 3H); 4.28 (septet, J=6.0 Hz, 1H); 6.80 (s, 1H); 6.97-7.04 (m, 2H); 7.53-7.60 (m, 2H); 7.68-7.72 (m, 2H); 7.93-7.97 (m, 2H).

Preparation of Compound (13)

Tert-butyl ester (13) was prepared from sulfonamide (9) (482 mg, 1.5 mmol) and alcohol (6) (310 mg, 1.0 mmol) following the procedure previously described for the preparation of compound (11), in Example 1. The crude reaction mixture was purified by flash chromatography (n-hexane/AcOEt=5:2), to give (13) (455 mg, 74% yield) as a yellow oil.

¹H-NMR (CDCl₃) δ: 1.21-1.32 (m, 15H); 1.90-2.10 (m, 2H); 3.10-3.50 (m, 2H); 3.86 (s, 3H); 4.06-4.16 (m, 1H); 4.43 (septet, J=6.2 Hz, 1H); 5.08 (s, 2H); 6.97-7.02 (m, 2H); 7.34 (m, 5H); 7.51-7.56 (m, 2H); 7.65-7.70 (m, 2H); 7.90-7.94 (m, 2H).

Preparation of Compound (16)

Following a procedure analogous to that used for the preparation of compound (15), ester (13) (450 mg, 0.73 mmol) was hydrogenated in the presence of 10% Pd—C to give (16) (428 mg, 100% yield).

¹H-NMR (CDCl₃) δ: 1.15-1.27 (m, 15H); 2.04-2.10 (m, 2H); 3.06 (m, 2H); 3.86 (s, 3H); 4.27 (m, 1H); 4.41 (septet, J=6.2 Hz, 1H); 6.98-7.02 (m, 2H); 7.52-7.56 (m, 2H); 7.68-7.72 (m, 2H); 7.95-7.99 (m, 2H).

Preparation of Compound (21)

Following a procedure analogous to that used for the preparation of compound (17), in Example 2, ester (16) (215 mg, 0.40 mmol) was acylated with acetyl chloride. Silica gel column chromatography (n-hexane/AcOEt=2:3) yielded the desired product (86 mg, 42% yield).

¹H-NMR (CDCl₃) δ: 1.19-1.25 (m, 15H); 1.90-2.04 (m, 5H); 3.13-3.50 (m, 2H); 3.87 (s, 3H); 4.12 (m, 1H); 4.41 (septet, 1H); 6.99-7.03 (m, 2H); 7.53-7.57 (m, 2H); 7.69-7.73 (m, 2H); 7.91-7.95 (m, 2H).

Preparation of Compound (27)

Following a procedure analogous to that used for the preparation of compound (35), in Example 1, ester (21) (81 mg, 0.15 mmol) was treated with TFA to give the desired carboxylic acid (27) (50 mg, 67% yield), after recrystallization from Et₂O and n-hexane.

¹H-NMR (CDCl₃) δ: 1.15-1.22 (m, 6H); 1.88-2.05 (m, 5H); 3.19-3.35 (m, 2H); 3.84 (s, 3H); 4.24 (t, 1H); 4.37 (septet, 1H); 6.30 (brs, 1H); 6.96-7.00 (m, 2H); 7.53-7.58 (m, 2H); 7.67-7.71 (m, 2H); 7.89-7.94 (m, 2H).

Preparation of Compound (33)

Following a procedure analogous to that used for the preparation of compound (37), in Example 1, carboxylic acid (27) (50 mg, 0.10 mmol) was coupled with O-(tert-butyldimethylsilyl)hydroxylamine. Silica gel column chromatography (n-hexane/AcOEt=1:2) yielded the desired product (45 mg, 71% yield).

¹H-NMR (CDCl₃) δ: 0.15 (s, 6H); 0.92 (s, 9H); 1.23-1.27 (m, 6H); 1.91-2.00 (m, 5H); 3.00-3.20 (m, 2H); 3.87 (s, 3H); 4.06-4.13 (m, 1H); 4.43 (septet, 1H); 5.89 (brs, 1H); 6.98-7.03 (m, 2H); 7.56-7.60 (m, 2H); 7.72-7.76 (m, 2H); 7.88-7.93 (m, 2H); 8.80 (brs, 1H).

Preparation of the Title Compound (1f)

Following a procedure analogous to that used for the preparation of compound (1a), tert-butyl O-silylate (33) (43 mg, 0.07 mmol) was treated with TFA to give the desired hydroxamic acid (31 mg, 90% yield), after recrystallization from Et₂O and n-hexane.

Mp=83-85° C.;

¹H-NMR (CDCl₃) δ: 1.20-1.26 (m, 6H); 1.94-2.04 (m, 5H); 3.02-3.40 (m, 2H); 3.86 (s, 3H); 4.22 (m, 1H); 4.45 (septet, 1H); 6.09 (brs, 1H); 6.98-7.02 (m, 2H); 7.55-7.59 (m, 2H); 7.71-7.75 (m, 2H); 7.89-7.94 (m, 2H).

Example 7

Preparation of Compound (1g): (R)—N-hydroxy-2-(N-isopropoxy-4'-methoxybiphenyl-4-ylsulfonamido)-4-(2-phenylacetamido)butanamide Preparation of Compound (22)

Following a procedure analogous to that used for the preparation of compound (17), in Example 2, ester (16) (200 mg, 0.37 mmol) was acylated with phenylacetyl chloride. Silica gel column chromatography (n-hexane/AcOEt=3:2) yielded the desired product (53 mg, 24% yield).

¹H-NMR (CDCl₃) δ: 1.16-1.25 (m, 15H); 1.90-2.05 (m, 2H); 3.12 (m, 2H); 3.57 (s, 2H); 3.87 (s, 3H); 3.94 (t, J=7.5 Hz, 1H); 4.37 (septet, 1H); 6.98-7.04 (m, 2H); 7.31-7.37 (m, 5H); 7.52-7.57 (m, 2H); 7.64-7.68 (m, 2H); 7.77-7.81 (m, 2H).

Preparation of Compound (28)

Following a procedure analogous to that used for the preparation of compound (35), in Example 1, ester (22) (48 mg, 0.08 mmol) was treated with TFA to give the desired carboxylic acid (28) (46 mg, 100% yield).

¹H-NMR (CDCl₃) δ: 1.15 (d, J=1.8 Hz, 3H); 1.18 (d, J=1.8 Hz, 3H); 1.93-2.10 (m, 2H); 3.10 (m, 2H); 3.56 (s, 2H); 3.86 (s, 3H); 4.15 (m, 1H); 4.37 (septet, 1H); 6.98-7.02 (m, 2H); 7.30-7.39 (m, 5H); 7.54-7.58 (m, 2H); 7.63-7.67 (m, 2H); 7.80-7.84 (m, 2H).

Preparation of Compound (34)

Following a procedure analogous to that used for the preparation of compound (37), in Example 1, carboxylic acid (28) (42 mg, 0.07 mmol) was coupled with O-(tert-butyldimethylsilyl)hydroxylamine. Silica gel column chromatography (n-hexane/AcOEt=2:1) yielded the desired product (17 mg, 32% yield).

¹H-NMR (CDCl₃) δ: 0.15 (s, 6H); 0.92 (s, 9H); 1.17-1.25 (m, 6H); 1.91-1.95 (m, 2H); 3.00-3.20 (m, 2H); 3.50 (s, 2H); 3.87 (s, 3H); 4.01-4.06 (m, 1H); 4.39 (septet, 1H); 5.75 (brs, 1H); 6.98-7.02 (m, 2H); 7.21-7.34 (m, 5H); 7.54-7.59 (m, 2H); 7.67-7.71 (m, 2H); 7.82-7.87 (m, 2H).

Preparation of the Title Compound (1g)

Following a procedure analogous to that used for the preparation of compound (1a), tert-butyl O-silylate (34) (15 mg, 0.02 mmol) was treated with TFA to give the desired hydroxamic acid (10 mg, 77% yield), after recrystallization from Et₂O and n-hexane.

¹H-NMR (CDCl₃) δ: 1.19-1.22 (m, 6H); 1.94-1.98 (m, 2H); 3.00-3.20 (m, 2H); 3.51 (s, 2H); 3.86 (s, 3H); 4.10-4.16 (m, 1H); 4.41 (septet, 1H); 5.89 (brs, 1H); 6.97-7.01 (m, 2H); 7.21-7.32 (m, 5H); 7.53-7.57 (m, 2H); 7.65-7.69 (m, 2H); 7.83-7.87 (m, 2H).

Example 8

Preparation of Compound (1h): (R)-benzyl 4-(hydroxyamino)-4-oxo-3-(N-(2-(2-(piperazin-1-yl)ethoxy)ethoxy)biphenyl-4-ylsulfonamido)butylcarbamate Preparation of Compound (61)

To a solution of 1-[2-(2-hydroxyethoxy)ethyl]piperazine (60) (5.0 g, 28.7 mmol) in CH₂Cl₂ (20 mL) wad added dropwise a solution of di-tert-butyldicarbonate (6.9 g, 31.5 mmol) in CH₂Cl₂ (20 mL) at 0° C. After stirring at room temperature for 12 h, the solution was diluted with Et₂O, washed with a saturated solution of NaHCO₃, with brine, dried (Na₂SO₄) and concentrated to yield the Boc-protected derivative (61) (7.2 g, 92% yield).

¹H-NMR (CDCl₃) δ: 1.43 (s, 9H); 2.45 (t, J=4.9 Hz, 4H); 2.57 (t, J=5.3 Hz, 2H); 3.44 (t, J=5.1 Hz, 4H); 3.56-3.67 (m, 6H); 4.17 (t, J=5.6 Hz, 1H).

¹³C-NMR (CDCl₃) δ: 28.47; 43.46; 53.16; 57.97; 61.86; 67.69; 72.44; 79.69; 155.00

Preparation of Compound (62)

Diethyl azodicarboxylate (DEAD) (2.15 mL, 13.65 mmol) was added dropwise to a solution containing alcohol (61) (2.50 g, 9.10 mmol), N-hydroxyphthalimide (1.48 g, 9.10 mmol) and triphenylphosphine (3.58 g, 13.6 mmol) in anhydrous THF (100 mL), under nitrogen atmosphere. The resulting solution was stirred overnight at rt and evaporated under reduced pressure to afford a crude product, which was purified by flash chromatography on silica gel (n-hexane/AcOEt=4:1) to yield (62) (4.30 g, 98% yield) as a pure yellow oil.

¹H-NMR (CDCl₃) δ: 1.44 (s, 9H); 2.38 (t, J=4.9 Hz, 4H); 2.50 (t, J=5.6 Hz, 2H); 3.39 (t, J=5.3 Hz, 4H); 3.64 (t, J=5.6 Hz, 2H); 3.82 (t, J=4.2 Hz, 2H); 4.37 (t, J=4.3 Hz, 2H); 7.72-7.86 (m, 4H).

Preparation of Compound (55)

Hydrazine hydrate (1.73 mL, 35.87 mmol) was added to a solution of compound (62) (4.30 g, 10.25 mmol) in ethanol (210 mL). After stirring at room temperature for 14 h the mixture was filtered and the filtrate concentrated. The residue was diluted with AcOEt, the precipitate was removed by filtration and the filtrate was evaporated to yield the desired O-alkylhydroxylamine (55) (2.15 g, 72.6% yield).

¹H-NMR (CDCl₃) δ: 1.45 (s, 9H); 2.45 (t, J=4.9 Hz, 4H); 2.61 (t, J=5.8 Hz, 2H); 3.43 (t, J=5.1 Hz, 4H); 3.58-3.65 (m, 4H); 3.80-3.85 (m, 2H).

Preparation of Compound (10)

Following a procedure analogous to that used for the preparation of compound (7), in Example 1, O-alkylhydroxylamine (55) (2.85 g, 9.86 mmol) was reacted with biphenyl-4-sulfonyl chloride (56). Silica gel column chromatography (AcOEt) yielded the desired sulfonamide (3.05 g, 61% yield).

¹H-NMR (CDCl₃) δ: 1.44 (s, 9H); 2.44 (t, J=4.9 Hz, 4H); 2.58 (t, J=5.6 Hz, 2H); 3.43 (t, J=5.3 Hz, 4H); 3.61 (t, J=5.5 Hz, 2H); 3.67-3.71 (m, 2H); 4.10-4.15 (m, 2H); 7.41-7.53 (m, 3H); 7.58-7.63 (m, 2H); 7.71-7.75 (m, 2H); 7.97-8.01 (m, 2H).

Preparation of Compound (14)

Tert-butyl ester (14) was prepared from sulfonamide (10) (1.18 g, 2.33 mmol) and alcohol (6) following the procedure previously described for the preparation of compound (11), in Example 1. The crude reaction mixture was purified by flash chromatography (n-hexane/AcOEt=1:5), to give the desired product (1.39 g, 75% yield) as a yellow oil.

¹H-NMR (CDCl₃) δ: 1.33 (s, 9H); 1.43 (s, 9H); 1.74-1.98 (m, 2H); 2.42 (m, 4H); 2.58 (t, J=5.3 Hz, 2H); 3.12-3.26 (m, 2H); 3.40 (m, 4H); 3.56-3.65 (m, 4H); 4.09-4.41 (m, 3H); 5.05 (s, 2H); 5.22 (br s, 1H); 7.32 (m, 5H); 7.40-7.74 (m, 7H); 7.96-8.00 (m, 2H).

Preparation of Compound (36)

Following a procedure analogous to that used for the preparation of compound (35), in Example 1, ester (14) (1.39 g, 1.74 mmol) was treated with TFA to give the desired carboxylic acid (36) (1.30 g, 86% yield), after recrystallization from Et₂O.

¹H-NMR (CDCl₃) δ: 1.80-2.05 (m, 2H); 3.19-3.29 (m, 6H); 3.40 (m, 4H); 3.62 (m, 10H); 4.15 (m, 2H); 4.29 (t, J=6.5 Hz, 1H); 5.01 (s, 2H); 5.35 (brs, 1H); 7.29 (m, 5H); 7.43-7.52 (m, 3H); 7.57-7.63 (m, 2H); 7.70-7.74 (m, 2H); 7.90-7.94 (m, 2H).

Preparation of the Title Compound (1h)

Following a procedure analogous to that used for the preparation of compound (37), in Example 1, carboxylic acid (36) (0.14 g, 0.16 mmol) was coupled with O-(tert-butyldimethylsilyl)hydroxylamine. Silica gel column chromatography (CHCl₃/MeOH=9:1) yielded the desired hydroxamic acid (13 mg, 12% yield).

¹H-NMR (CDCl₃) δ: 1.80-2.00 (m, 2H); 2.47-3.17 (m, 16H); 4.13 (m, 3H); 4.92 (s, 2H); 6.25 (brs, 1H); 7.18 (m, 5H); 7.38-7.64 (m, 7H); 7.96 (m, 2H).

Example 9

Preparation of Compound (2): (R)-4-(1,3-dioxoisoindolin-2-yl)-N-hydroxy-2-(N-isopropoxy-4'-methoxybiphenyl-4-ylsulfonamido)butanamide Preparation of Compound (40)

Following a procedure analogous to that used for the preparation of compound (6), in Example 1, (S)-α-hydroxy-1,3-dioxo-2-isoindolinebutyric acid (39) (1.0 g, 4.0 mmol) was treated with N,N-dimethylformamide di-tert-butyl acetal. Silica gel column chromatography (n-hexane/AcOEt=3:2) yielded the desired ester (530 mg, 43% yield), as a white solid.

Mp=122-123° C.;

¹H-NMR (CDCl₃) δ: 1.46 (s, 9H); 1.87-2.23 (m, 2H); 3.02 (d, J=5.3 Hz, 1H); 3.86 (t, J=7.3 Hz, 2H); 4.07-4.16 (m, 1H); 7.69-7.75 (m, 2H); 7.80-7.87 (m, 2H).

Preparation of Compound (43)

Tert-butyl ester (43) was prepared from sulfonamide (9) (400 mg, 1.24 mmol) and alcohol (40) (250 mg, 0.82 mmol) following the procedure previously described for the preparation of compound (11). The crude reaction mixture was purified by flash chromatography (n-hexane/AcOEt=2:1), to give the desired product (217 mg, 43% yield).

¹H-NMR (CDCl₃) δ: 1.24-1.29 (m, 15H); 2.10-2.30 (m, 2H); 3.51-3.74 (m, 2H); 3.87 (s, 3H); 4.06-4.23 (m, 1H); 4.46 (septet, 1H); 6.98-7.03 (m, 2H); 7.52-7.88 (m, 10H).

Preparation of Compound (46)

Following a procedure analogous to that used for compound (35), ester (43) (205 mg, 0.33 mmol) was treated with TFA to give the desired carboxylic acid (46) (135 mg, 74% yield), after recrystallization from Et₂O.

Mp=185-187° C.;

¹H-NMR (CDCl₃) δ: 1.21 (d, J=6.2 Hz, 3H); 1.27 (d, J=6.2 Hz, 3H); 2.10-2.28 (m, 2H); 3.61 (m, 2H); 3.87 (s, 3H); 4.33 (m, 1H); 4.46 (septet, 1H); 6.98-7.02 (m, 2H); 7.50-7.54 (m, 4H); 7.65-7.85 (m, 6H).

Preparation of Compound (48)

Following a procedure analogous to that used for the preparation of compound (37), carboxylic acid (46) (130 mg, 0.23 mmol) was coupled with O-(tert-butyldimethyl-silyl)hydroxylamine. Silica gel column chromatography (n-hexane/AcOEt=3:2) yielded the desired product (110 mg, 70% yield).

¹H-NMR (CDCl₃) δ: 0.26 (s, 6H); 1.00 (s, 9H); 1.23 (d, J=6.2 Hz, 3H); 1.30 (d, J=6.2 Hz, 3H); 2.15-2.30 (m, 2H); 3.30-3.60 (m, 2H); 3.89 (s, 3H); 4.03 (m, 1H); 4.43 (septet, 1H); 6.98-7.02 (m, 2H); 7.16 (m, 2H); 7.36-7.41 (m, 2H); 7.61 (m, 4H); 7.68-7.72 (m, 2H); 8.72 (brs, 1H).

Preparation of Compound (2)

Following a procedure analogous to that used for the preparation of compound (1a), tert-butyl O-silylate (48) (100 mg, 0.14 mmol) was treated with TFA to give the desired hydroxamic acid (61 mg, 77%), after recrystallization from Et₂O and n-hexane. Mp=75-76° C.;

¹H-NMR (CDCl₃) δ: 1.23 (d, J=6.2 Hz, 3H); 1.30 (d, J=6.2 Hz, 3H); 2.12-2.32 (m, 2H); 3.40-3.53 (m, 2H); 3.88 (s, 3H); 4.02-4.20 (m, 1H); 4.46 (septet, 1H); 6.98-7.02 (m, 2H); 7.29-7.39 (m, 2H); 7.42-7.46 (m, 2H); 7.63 (m, 4H); 7.72-7.76 (m, 2H).

Example 10

Preparation of Compound (3) (R)-4-(1,3-dioxoisoindolin-2-yl)-N-hydroxy-2-(N-isopropoxy-4-phenoxyphenylsulfonamido)butanamide Preparation of Compound (41)

Following a procedure analogous to that used for the preparation of compound (7), O-isopropylhydroxylamine (54) (415 mg, 3.72 mmol) was reacted with 4-phenoxybenzenesulfonyl chloride (58) to give the desired sulfonamide (41) (989 mg, 86% yield).

¹H-NMR (CDCl₃) δ: 1.19 (d, J=6.2 Hz, 6H); 4.25 (septet, J=6.2 Hz, 1H); 6.71 (s, 1H); 7.03-7.10 (m, 4H); 7.19-7.27 (m, 1H); 7.38-7.46 (m, 2H); 7.83-7.88 (m, 2H).

Preparation of Compound (44)

Tert-butyl ester (44) was prepared from sulfonamide (41) (378 mg, 1.23 mmol) and alcohol (40) following the procedure previously described for compound (11). The crude reaction mixture was purified by flash chromatography (n-hexane/AcOEt=7:2), to give the desired product (253 mg, 51% yield).

$^1$H-NMR (CDCl$_3$) δ: 1.18-1.45 (m, 15H); 1.99-2.38 (m, 2H); 3.56-3.74 (m, 2H); 4.06-4.15 (m, 1H); 4.43 (septet, J=6.2 Hz, 1H); 6.94-6.98 (m, 2H); 7.09-7.12 (m, 2H); 7.21-7.28 (m, 2H); 7.39-7.47 (m, 2H); 7.67-7.83 (m, 5H).

Preparation of Compound (47)

Following a procedure analogous to that used for the preparation of compound (35), ester (44) (250 mg, 0.42 mmol) was treated with TFA to give the desired carboxylic acid (47) (164 mg, 71%), after recrystallization from Et$_2$O and n-hexane.

$^1$H-NMR (CDCl$_3$) δ: 1.20 (d, J=6.2 Hz, 3H); 1.25 (d, J=6.2 Hz, 3H); 2.10-2.30 (m, 2H); 3.55-3.75 (m, 2H); 4.25-4.35 (m, 1H); 4.44 (septet, J=6.2 Hz, 1H); 6.88-6.92 (m, 2H); 7.09-7.13 (m, 2H); 7.21-7.28 (m, 2H); 7.39-7.47 (m, 2H); 7.69-7.84 (m, 5H).

Preparation of Compound (49)

Following a procedure analogous to that used for the preparation of compound (37), carboxylic acid (47) (160 mg, 0.30 mmol) was coupled with O-(tert-butyldimethyl-silyl)hydroxylamine to give the desired product (178 mg, 87% yield).

$^1$H-NMR (CDCl$_3$) δ: 0.26 (s, 6H); 1.00 (s, 9H); 1.21 (d, J=6.2 Hz, 3H); 1.26 (d, J=6.2 Hz, 3H); 2.10-2.31 (m, 2H); 3.40-3.65 (m, 2H); 3.90-4.10 (m, 1H); 4.40 (septet, J=6.2 Hz, 1H); 6.59 (brs, 1H); 7.08-7.13 (m, 2H); 7.22-7.30 (m, 2H); 7.41-7.49 (m, 2H); 7.58-7.62 (m, 2H); 7.69-7.83 (m, 5H).

Preparation of the Title Compound (3)

Following a procedure analogous to that used for the preparation of compound (1a), tert-butyl O-silylate (49) (170 mg, 0.25 mmol) was treated with TFA to give the desired hydroxamic acid (3) (97 mg, 68% yield), after recrystallization from Et$_2$O and n-hexane.

$^1$H-NMR (CDCl$_3$) δ: 1.22 (d, J=6.2 Hz, 3H); 1.26 (d, J=6.2 Hz, 3H); 2.07-2.28 (m, 2H); 3.43-3.65 (m, 2H); 4.05-4.20 (m, 1H); 4.44 (septet, J=6.2 Hz, 1H); 6.70-6.83 (m, 2H); 7.09-7.13 (m, 2H); 7.22-7.29 (m, 2H); 7.40-7.48 (m, 2H); 7.64-7.83 (m, 5H).

Example 11

Preparation of Compound (4) (R)-4-(1,3-dioxoisoindolin-2-yl)-2-(4'-ethoxy-N-isopropoxybiphenyl-4-ylsulfonamido)-N-hydroxybutanamide Preparation of Compound (42)

Following a procedure analogous to that used for the preparation of compound (7), O-isopropylhydroxylamine (54) (436 mg, 3.91 mmol) was reacted with 4-bromobenzenesulfonyl chloride (59) to give the desired sulfonamide (42) (870 mg, 75%).

$^1$H-NMR (CDCl$_3$) δ: 1.18 (d, J=6.2 Hz, 6H); 4.25 (septet, J=6.2 Hz, 1H); 6.80 (s, 1H); 7.66-7.70 (m, 2H); 7.75-7.80 (m, 2H).

Preparation of Compound (45)

Tert-butyl ester (45) was prepared from sulfonamide (42) (864 mg, 2.94 mmol) and alcohol (40) following the procedure previously described for the preparation of compound (11). The crude reaction mixture was purified by flash chromatography (n-hexane/AcOEt=5:1), to give the desired product (720 mg, 63% yield).

$^1$H-NMR (CDCl$_3$) δ: 1.19-1.40 (m, 15H); 2.05-2.20 (m, 2H); 3.55-3.80 (m, 2H); 4.02-4.20 (m, 1H); 4.43 (septet, J=6.2 Hz, 1H); 7.60-7.76 (m, 6H); 7.80-7.87 (m, 2H).

Preparation of Compound (50)

A mixture of ester (45) (200 mg, 0.34 mmol), 4-ethoxyphenylboronic acid (96 mg, 0.58 mmol), Pd(PPh$_3$)$_4$ (20 mg, 0.017 mmol) and K$_3$PO$_4$ (166 mg, 0.78 mmol) in 4.5 mL dioxane/H$_2$O 5:1 was heated to 85° C. under nitrogen. After 2 h, the reaction mixture was diluted with sat. solution of NaHCO$_3$, extracted with ACOEt and dried over Na$_2$SO$_4$. The organic layer was concentrated in vacuo and the crude product was purified by flash chromatography on silica gel (n-hexane/AcOEt=4:1) to give (50) (193 mg, 88% yield).

$^1$H-NMR (CDCl$_3$) δ: 1.20-1.39 (m, 15H); 1.45 (t, J=6.9 Hz, 3H); 2.04-2.35 (m, 2H); 3.50-3.80 (m, 2H); 4.05-4.15 (m, 3H); 4.46 (septet, J=6.2 Hz, 1H); 6.97-7.01 (m, 2H); 7.51-7.88 (m, 10H).

Preparation of Compound (51)

Following a procedure analogous to that used for the preparation of compound (35), ester (50) (193 mg, 0.30 mmol) was treated with TFA to give the desired carboxylic acid (51) (150 mg, 87%), after recrystallization from Et$_2$O and n-hexane.

$^1$H-NMR (CDCl$_3$) δ: 1.21 (d, J=6.2 Hz, 3H); 1.24 (d, J=6.2 Hz, 3H); 1.46 (t, J=6.9 Hz, 3H); 2.10-2.30 (m, 2H); 3.50-3.75 (m, 2H); 4.10 (q, J=6.9 Hz, 2H); 4.22-4.50 (m, 2H); 6.97-7.01 (m, 2H); 7.48-7.53 (m, 4H); 7.65-7.85 (m, 6H).

Preparation of Compound (52)

Following a procedure analogous to that used for the preparation of compound (37), carboxylic acid (51) (140 mg, 0.25 mmol) was coupled with O-(tert-butyldimethyl-silyl)hydroxylamine. Silica gel column chromatography (n-hexane/AcOEt=2:1) yielded the desired product (120 mg, 71% yield).

$^1$H-NMR (CDCl$_3$) δ: 0.26 (s, 6H); 1.00 (s, 9H); 1.23 (d, J=6.2 Hz, 3H); 1.30 (d, J=6.2 Hz, 3H); 1.47 (t, J=6.9 Hz, 3H); 2.10-2.30 (m, 2H); 3.30-3.60 (m, 2H); 3.90-4.05 (m, 1H); 4.11 (q, J=6.9 Hz, 2H); 4.43 (septet, J=6.2 Hz, 1H); 6.99-7.01 (m, 2H); 7.10-7.22 (m, 2H); 7.35-7.39 (m, 2H); 7.60-7.71 (m, 6H); 8.70 (brs, 1H).

Preparation of the title compound (4) Following a procedure analogous to that used for the preparation of compound (1a), tert-butyl O-silylate (52) (120 mg, 0.17 mmol) was treated with TFA to give the desired hydroxamic acid (4) (83 mg, 82%), after recrystallization from Et$_2$O and n-hexane.

$^1$H-NMR (CDCl$_3$) δ: 1.24 (d, J=6.2 Hz, 3H); 1.30 (d, J=6.2 Hz, 3H); 1.46 (t, J=6.9 Hz, 3H); 2.10-2.35 (m, 2H); 3.40-3.60 (m, 2H); 4.05-4.16 (m, 3H); 4.46 (septet, J=6.2 Hz, 1H); 6.96-7.01 (m, 2H); 7.31-7.44 (m, 4H); 7.63-7.75 (m, 6H).

Example 12

Preparation of Compound (64): benzyl 3-(N-isopropoxybiphenyl-4-ylsulfonamido)propylcarbamate Carbamate (64) was prepared from sulfonamide (8) (400 mg, 1.37 mmol) and commercial alcohol (63) following the procedure previously described for the preparation of compound (11). The crude reaction mixture was purified by flash chromatography (n-hexane/AcOEt=3:1), to give the desired product (400 mg, 87% yield).

$^1$H-NMR (CDCl$_3$) δ: 1.23-1.27 (m, 8H); 1.76-1.89 (m, 2H); 3.30 (q, J=62 Hz, 2H); 4.54 (septet, J=6.2 Hz, 1H); 5.08 (s, 2H); 7.34 (m, 5H); 7.41-7.53 (m, 3H); 7.59-7.63 (m, 2H); 7.72-7.76 (m, 2H); 7.88-7.93 (m, 2H)

Example 13

Preparation of Compound (1i)

Preparation of Compound (65)

To a solution of compound (55) of example 8 (1.76 g; 6 mmol) in THF (15 ml) at 0° C. was added N-methylmorpholine (0.66 ml, 6 mmol) and a solution of 4'-methoxy[1,1'-biphenyl]-4-sulfonyl chloride (1.69 g, 6 mmol) in THF (15 ml). The reaction mixture was stirred at room temperature for 3 days, then concentrated. The residue was taken up with ethyl acetate, washed with water and the organic phase was concentrated to obtain an orange oil. The crude product was purified by flash chromatography (EtOAc) to give compound (65) as a yellow oil in 75% yield.

1H-NMR (CDCl$_3$, 200 MHz): 7.95 (d, 2H); 7.68 (d, 2H); 7.55 (d, 2H); 7.0 (d, 2H); 4.12 (m, 2H); 3.86 (s, 3H); 3.67 (m,

4H); 3.6 (m, 4H); 3.42 (t, J=5.3 Hz, 4H); 2.56 (t, J=5.6 Hz, 2H); 2.42 (t, J=4.95 Hz, 4H); 1.44 (s, 9H).

Preparation of Compound (66)

DEAD (0.153 ml, 0.97 mmol) was added dropwise, at 0° C., to a solution of sulfonamide (65) (458.8 mg; 0.97 mmol), compound (6) of example 1 (300 mg, 0.97 mmol) and triphenylphosphine (255 mg; 0.97 mmol) in dry THF (16 ml).

The mixture was stirred at room temperature overnight then concentrated and purified by flash chromatography (hexane/ethyl acetate 1/5) to give compound (66) as an oil in 70% yield.

1H-NMR (CDCl$_3$, 200 MHz): 7.95 (d, J=8.6 Hz, 2H); 7.57 (m, 4H); 7.26 (s, 5H); 7.0 (d, J=8.8 Hz, 2H); 5.18 (m, 1H); 5.06 (s, 2H); 4.33 (m, 1H); 4.14 (m, 2H); 3.87 (s, 3H); 3.62 (m, 4H); 3.39 (m, 4H); 3.21 (m, 2H); 2.56 (t, J=5.4 Hz, 2H); 2.4 (m, 4H); 1.92 (m, 2H); 1.44 (s, 9H), 1.34 (s, 9H).

Preparation of Compound (1i)

To a solution of tert-Butyl ester (66) (800 mg, 0.966 mmol) in dry CH$_2$Cl$_2$ (12 ml), TFA (7.4 ml, 96.6 mmol) was added dropwise at 0° C. The reaction mixture was stirred at 0° C. for 1 h and then 4 h at room temperature. The solvent and TFA were removed in vacuo to give carboxylic acid (1i), as di-trifluoroacetate salt, as a white foam in 79% yield.

1H-NMR (CDCl$_3$, 200 MHz): 9.45 (bs, $^+$NH$_2$, $^+$NH); 8.0 (d, J=7.8 Hz, 2H); 7.68 (m, 4H); 7.4 (s, 5H); 7.1 (d, J=8.2 Hz, 2H); 5.6 (s, 1H); 5.13 (s, 2H); 4.27 (m, 3H); 3.97 (s, 3H); 3.78 (m, 10H); 3.44 (m, 4H); 1.98 (m, 2H).

Example 14

Preparation of Compound (1j)

To a solution of acid (1i) (150 mg, 0.167 mmol) in dry CH$_2$Cl$_2$ (4 ml) was added O-(tert-Butyldimethylsilyl)hydroxylamine (79 mg, 0.534 mmol) and EDCI (96 mg, 0.501 mmol). The reaction mixture was stirred at room temperature for 5 h then concentrated and the residue was dissolved in EtOAc and washed with water. The organic phase was dried (Na$_2$SO$_4$) and evaporated in vacuo. Thus obtained white solid (140 mg) was dissolved in dry CH$_2$Cl$_2$ (3 ml) and treated with TFA (0.8 ml). The reaction mixture was stirred at 0° C. for 1 h then allowed to reach room temperature and stirred for 4 h. The solution was concentrated to obtain a brown oil that was triturated with a mixture of CH$_2$Cl$_2$/Et$_2$O to give a brown solid hydroxamic acid (1j), as di-trifluoroacetate, in 50% yield.

1H-NMR (CDCl$_3$, 200 MHz): 7.86 (d, J=7.2 Hz, 2H); 7.56 (m, 4H); 7.24 (s, 5H); 6.94 (d, J=8.2 Hz, 2H); 5.73 (s, 1H); 5.1 (s, 2H); 4.1 (m, 4H); 3.82 (s, 3H); 3.53 (m, 8H); 3.25 (m, 4H); 2.05 (m, 2H).

Example 15

Preparation of Compound (1k)

To a solution of (1j) (40 mg, 0.04 mmol) in dry DMSO (1 ml) was added 2,5-dioxipyrrolidine-1-yl propionate (10 mg, 0.534 mmol) and TEA (10 drops, pH=8). The reaction mixture was stirred at room temperature for 24 h then were added 10 ml of Et$_2$O. The reaction was stopped and the solution cooled to −15° C. then left to reach 0° C. The ethyl ether layer was decanted and the residual yellow oil concentrated in vacuo. The pure compound (1k) was obtained after chromatography (CH$_2$Cl$_2$/MeOH) as a colorless oil in 24% yield.

1H-NMR (CDCl$_3$, 200 MHz): 7.88 (d, J=8.2 Hz, 2H); 7.6 (m, 4H); 7.26 (s, 5H); 6.96 (d, J=8.8 Hz, 2H); 5.09 (s, 2H); 4.34 (m, 3H); 3.87 (s, 3H); 3.62 (m, 6H); 3.45 (m, 4H); 2.59 (m, 2H); 2.46 (m, 4H); 2.28 (q, J=7.5 Hz, 2H); 1.68 (m, 2H); 1.11 (t, J=7.5 Hz, 3H).

Example 16

MMP Inhibition Assays

Recombinant human pro-MMP-2 was supplied by Prof. Gillian Murphy (Department of Oncology, University of Cambridge, UK), while pro-MMP-13 and pro-MMP-14 were purchased from Calbiochem. Proenzymes were activated immediately prior to use with p-aminophenylmercuric acetate (APMA: 2 mM for 1 h at 37° C. for pro-MMP-2 and 1 mM for 30 min at 37° C. for pro-MMP-13). Pro-MMP-14 was activated with trypsin 5 µg/ml for 15 min at 37° C. followed by soybean trypsin inhibitor (SBTI) 23, µg/ml. For assay measurements, the inhibitor stock solutions (DMSO, 100 mM) were further diluted, at seven different concentrations (0.01 nM-100 µM) for each MMP in the fluorimetric assay buffer (FAB: Tris 50 mM, pH=7.5, NaCl 150 mM, CaCl$_2$ 10 mM, Brij 35 0.05% and DMSO 1%). Activated enzyme (final concentration 2.9 nM for MMP-2, 1 nM for MMP-14, 0.33 nM for MMP-13) and inhibitor solutions were incubated in the assay buffer for 4 h at 25° C. After the addition of 200 µM solution of the fluorogenic substrate Mca-Lys-Pro-Leu-Gly-Leu-Dpa-Ala-Arg-NH$_2$ (Bachem) (see, for a reference, Neumann, U.; Kubota, H.; Frei, K.; Ganu, V.; Leppert, D. Anal. Biochem. 2004, 328, 166) for all of the enzymes in DMSO (final concentration 2 µM), the hydrolysis was monitored every 15 sec. for 20 min recording the increase in fluorescence ($\lambda_{ex}$=325 nm, $\lambda_{em}$=395 nm) using a Molecular Device SpectraMax Gemini XS plate reader.

The assays were performed in triplicate, in a total volume of 200 µl per well, in 96-well microtitre plates (Corning, black, NBS). Control wells lack inhibitor. The MMP inhibition activity was expressed in relative fluorescent units (RFU). Percent of inhibition was calculated from control reactions without the inhibitor. IC$_{50}$ was determined using the formula: $V_i/V_o = 1/(1+[I]/IC_{50})$, where V$_i$ is the initial velocity of substrate cleavage in the presence of the inhibitor at concentration [I] and V$_o$ is the initial velocity in the absence of the inhibitor. Results were analyzed using SoftMax Pro software and GraFit software.

TABLE 1

| Compound | IC$_{50}$ MMP-2 (nM) | IC$_{50}$ MMP-13 (nM) | IC$_{50}$ MMP-14 (nM) |
| --- | --- | --- | --- |
| Reference Compound (5b) | 8.4 ± 0.1 | 4.4 ± 0.5 | 240 ± 19 |
| 1b | 1.48 ± 0.17 | 4.6 ± 0.1 | 94 ± 2.8 |
| 1c | 0.98 ± 0.12 | 2.2 ± 0.3 | 95.5 ± 4.5 |
| 1d | 0.33 ± 0.02 | 0.68 ± 0.1 | 41.1 ± 1.16 |
| 1e | 1.43 ± 0.1 | 1.4 ± 0.1 | 80.7 ± 5.4 |
| 1f | 0.13 ± 0.03 | 0.58 ± 0.04 | 23.5 ± 2.2 |
| 1g | 0.37 ± 0.06 | 0.25 ± 0.02 | 24.7 ± 2.2 |
| 1j | 0.3 ± 0.03 | 0.2 ± 0.01 | 27 ± 1 |
| 2 | 0.67 ± 0.06 | 0.19 ± 0.01 | 3.90 ± 0.18 |

As clearly indicated in the above table 1, the compounds of formula (I) of the invention resulted to be endowed with a significant inhibitory activity against MMP-2, MMP-13 and MMP-14 and may be thus useful, in therapy, for the treatment of degenerative disorders involving those same enzymes.

Surprisingly, based on this highly sensible method for assessing the inhibitory activity against the tested enzymes, the compounds of the invention resulted to be endowed with an inhibitory activity markedly higher than that exerted by the structurally closest Reference Compound (5b) of the prior art. Interestingly, the inhibitory activity of the compounds of the invention resulted to be significantly higher than that of Reference Compound (5b), of at least one magnitude order, against MMP-2; a comparable inhibitory profile may be also observed when considering the inhibition of MMP-13 and MMP-14, though to a lesser extent. Moreover, such a profile is constantly shared and steadily observed within the whole class of the representative compounds of the invention being tested. Remarkably, apart from being particularly active in the inhibition of the above metalloproteases MMP-2, MMP-13 and MMP-14, each considered alone, the fact that the compounds of the invention are effective in the inhibition of all of these enzymes is particularly advantageous, in therapy, where it is known that they all play a role in the degenerative processes.

Example 17

In Vivo Inhibition Experiment

Compound (2), as a representative compound of the invention, was tested in an in vivo assay to evaluate its inhibitory activity on cancer cells. In particular, HUVEC cultures were purchased from Cascade Biologics (Portland, Oreg.) and cultured in gelatin-coated flasks using M199, 10% FCS (Fetal Calf Serum, Seromed, Milan, Italy) supplemented with FGF (Fibroblast Growth Factor, PeproTech, Inc., Rocky Hill, N.J.) (1 µg aFGF (acidic Fibroblast Growth Factor)+1 µg bFGF (basic Fibroblast Growth Factor)/100 ml medium), EGF (Epidermal Growth Factor) (1 µg/100 ml medium), heparin (10 mg/100 ml medium), (ICN Pharmaceuticals, Inc., Casta Mesa, Calif.), hydrocortisone (Sigma Chemical Co.) (0.1 mg/100 ml medium).
Growth Assay
At day 0 cells were plated in 96 microwell plates at 1000 cells in 200 µl of complete culture medium. The inhibitor was added to the cells at different concentrations (10, 100 µM). HUVEC were quantified at 24, 48 and 72 hrs. Indirect optical density (OD) quantification was obtained fixing/staining the cells for 20 minutes with a crystal violet solution [see, for a reference, Fassina, G. et al., Clin Cancer Res, (2004) 10, 4865-73].
Chemoinvasion
HUVEC invasion was assessed in Boyden chambers (Costar) using serum-free fibroblast conditioned medium (FB-CM) as chemoattractants. Cells were treated with the inhibitor at the indicated doses and incubated at 37° C. for 5 hours in humidified atmosphere. Cell invasion was assessed by densitometric scanning of whole filter surface. Each test was performed in triplicate and repeated three times [see, for a reference, Albini, A., et al., Int. J. Dev. Biol., (2004), 48, 563-71].
Morphogenesis on Matrigel
Matrigel was thawed at 4° C. in an ice-water bath, and 200 µl of a concentrated solution (10 mg/ml) were pipetted into 13 mm/diameter tissue culture wells, avoiding even small bubbles. The matrigel was then polymerized for 1 hr at 37° C. Once polymerization has occurred, 7×10⁴ cells in 1 ml of complete medium were carefully pipetted on top of the gel. The plates were then incubated at 37° C. in a 5% CO, humidified atmosphere. The assays were monitored and photographed with an inverted microscope.
Endothelial cells formed interconnected networks in the matrigel that was reduced by anti-angiogenic compounds (see, for a reference, the aforementioned Albini, A. et al.).
Results
The tested compound (2) both showed a time and dose dependent cell growth inhibition as compared to untreated controls. At the higher dose tested (100 µM) we observed a 100% inhibition starting from 48 hours of treatment. In the invasion assay compound (2), at the higher dose tested (100 µM), showed a significant inhibitory activity on endothelial cell migration through a reconstituted basement membrane. At high dose (100 µM), compound (2) started to show some pro-apoptotic activity. At 48 hours the compound showed the ability to induce programmed cell death. According to these evidences, compound (2) appeared to be particularly active as cancer cells activity inhibitor.

The invention claimed is:

1. A compound of formula (I)

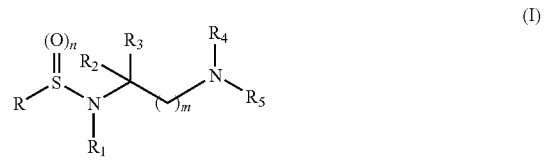

(I)

wherein:

R is a group of formula —Ar—X—Ar' (II) wherein Ar is an arylene group and Ar' is an aryl group; the said Ar and Ar' being optionally substituted by one or more groups selected from:

(i) straight or branched alkyl, alkoxy, hydroxyalkyl, alkoxyalkyl, aminoalkyl, alkylamino, aminoacyl, acylamino or perfluorinated alkyl, each of which having from 1 to 4 carbon atoms in the alkyl chain;

(ii) straight or branched $C_2$-$C_6$ alkenyl or alkynyl group; and (iii) halogen or a cyano (—CN) group;

X is a single bond or it is a divalent linker selected from a straight or branched $C_1$-$C_4$ alkylene chain, —O—, —S—, —S(O)$_2$—, —CO—, —NR'—, —NR'CO— and —CONR'—, wherein R' is H or a straight or branched $C_1$-$C_4$ alkyl group;

$R_1$ is —OH or a group —ORa wherein Ra is selected from straight or branched $C_1$-$C_4$ alkyl and $C_2$-$C_4$ alkenyl groups; or Ra is a group of formula (III)

—(CH$_2$)$_p$—Z—(CH$_2$)$_r$—W (III)

wherein p is zero or an integer from 1 to 4; Z is a single bond or a divalent linker selected from —O—, —NR'—, —NR'CO— and —CONR'—, wherein R' is as above defined; r is zero or an integer from 1 to 4; and W is phenyl or a 5 or 6 membered heterocycle, each of which being optionally substituted by one or more groups selected from —NH$_2$, —COR', —CONHR', —COOR', —SO$_2$NHR' wherein R' is as above defined, aryl heteroaryl or by one or more of the above groups from (i) to (ii);

One of $R_2$ and $R_3$ is H, and the other is a zinc binding group selected from —COOH, —COORb, —CONHOH, —CONHORb, —CONRbOH, —CONHS(O)$_2$Rb, —CONH$_2$, —CONHRb and —P(O)(OH)$_2$, wherein Rb is a straight or branched alkyl, arylalkyl or heteroarylalkyl group having from 1 to 4 carbon atoms in the alkyl chain; or any of the above $R_2$ or $R_3$ groups is linked to $R_1$ so as to form a 5 to 7 membered heterocyclic ring at least comprising two adjacent N—O heteroatoms, optionally substituted by one or more oxo groups (═O);

$R_4$ and $R_5$ together with the N atom to which they are bonded, form an optionally benzocondensed 4 to 6 membered heterocycle, optionally substituted by a group Ra as above defined and/or by one or more oxo (═O) groups;

n is 1 or 2;

m is an integer from 1 to 6;

or a pharmaceutically acceptable salt thereof.

2. A compound according to claim 1 wherein $R_4$ and $R_5$ together with the N atom to which they are bonded form an optionally benzocondensed 4 to 6 membered heterocycle selected from:

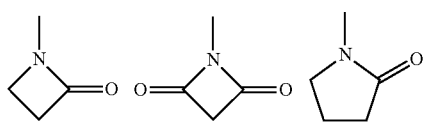
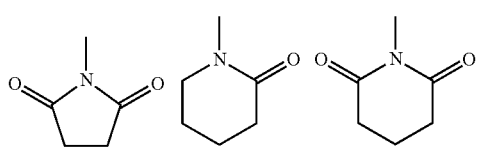
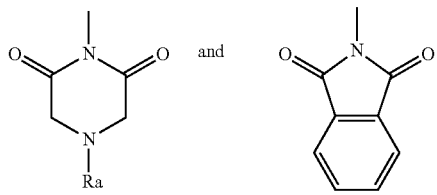
wherein Ra is as defined in claim 1.
3. A compound according to claim 1 wherein n and m are both 2.
4. A compound selected from the group consisting of
(1a)
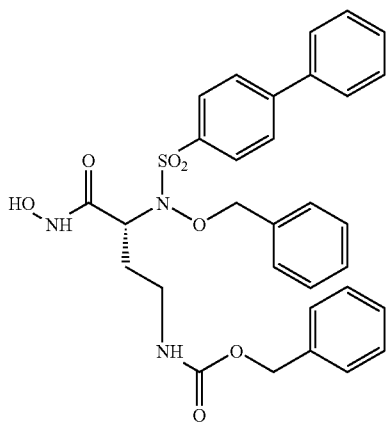
(1b)
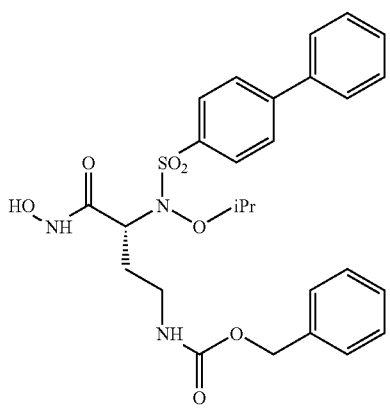
(1c)
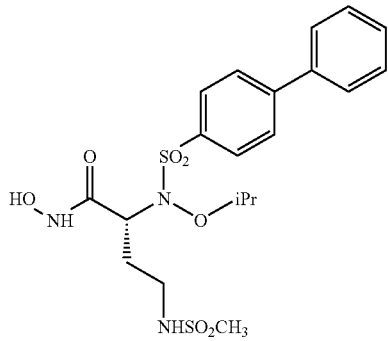
(1d)
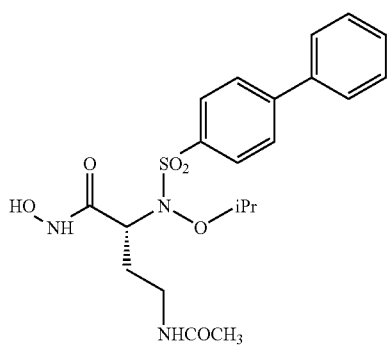
(1e)
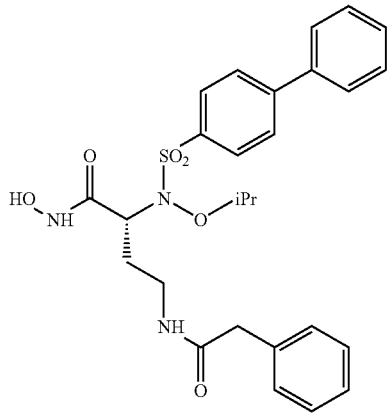
(1f)
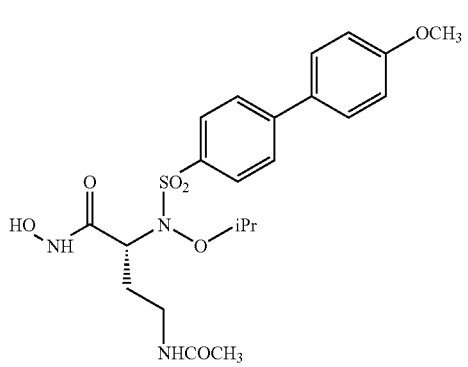

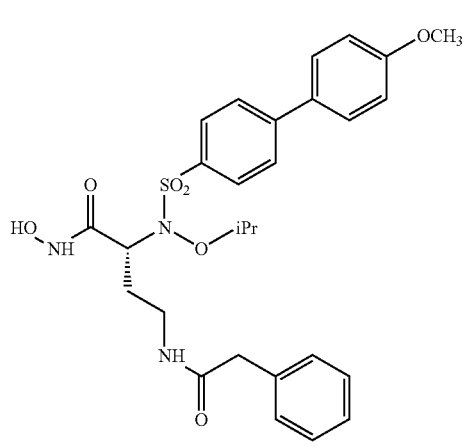
(1g)
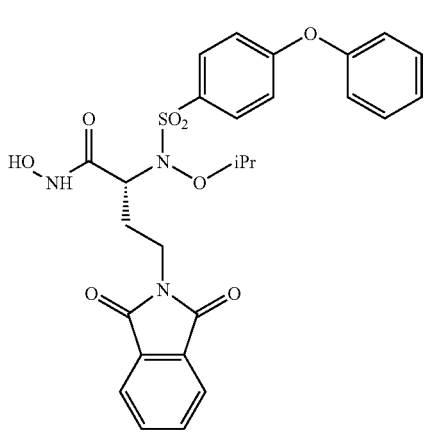
(3)
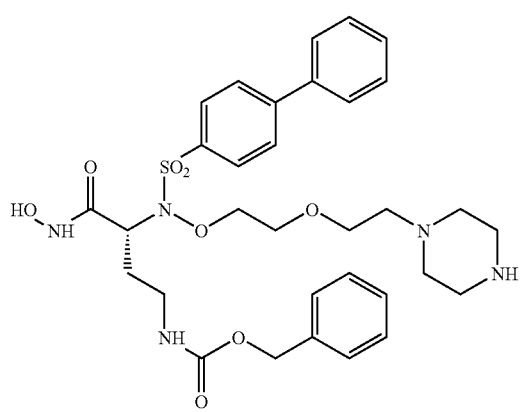
(1h)
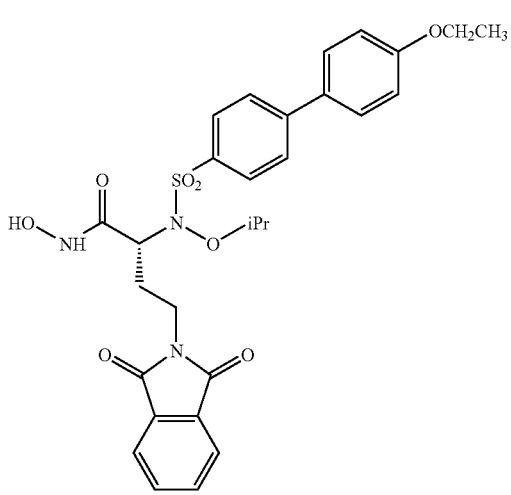
(4)
(2)
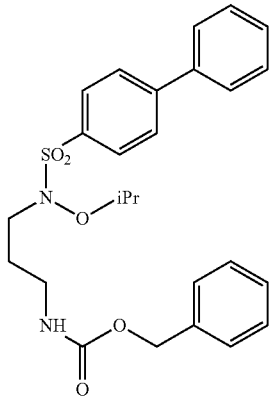
(64)

(1i)

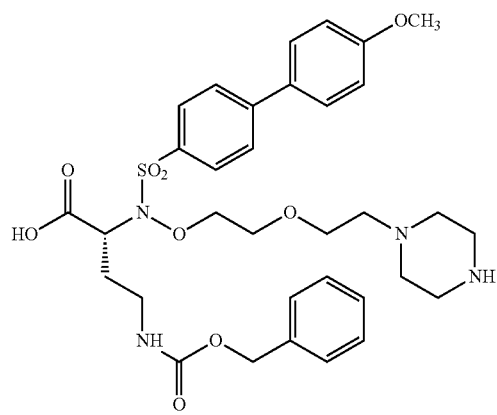

(1j)

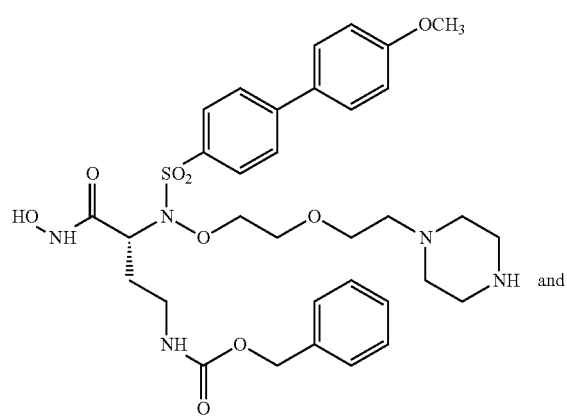

and (1k)

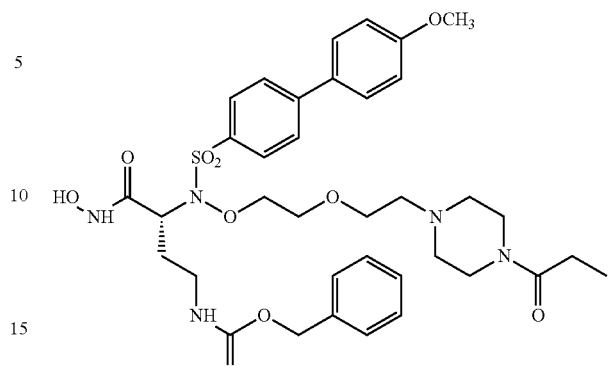

or a pharmaceutically acceptable salt thereof.

5. A pharmaceutical composition comprising, as an active ingredient, a pharmaceutically effective amount of a compound as defined in claim 1 or 4 in combination with one or more pharmaceutically acceptable carriers, diluents or excipients.

6. A method for the treatment of arthritis or sepsis which method comprises administering to a mammal in need thereof, a therapeutically effective amount of a compound as defined in any one of claims 1 or 4 or a pharmaceutically acceptable salt thereof.

* * * * *